US011540716B1

(12) United States Patent
Plath et al.

(10) Patent No.: US 11,540,716 B1
(45) Date of Patent: Jan. 3, 2023

(54) WEARABLE DEVICE FOR MONITORING THE HEALTH AND SUPERVISION OF A SUPERVISED PERSON AND RELATED SYSTEMS AND METHODS

(71) Applicant: Littlebird Connected Care, Inc., Yakima, WA (US)

(72) Inventors: Monica Marie Plath, Yakima, WA (US); Gadi Amit, San Mateo, CA (US); Stanislav Moiseyenko, San Rafael, CA (US); Christopher James Foster, San Francisco, CA (US); Tim Suleymanov, San Francisco, CA (US)

(73) Assignee: Littlebird Connected Care, Inc., Fall City, WA (US)

( * ) Notice: Subject to any disclaimer, the term of this patent is extended or adjusted under 35 U.S.C. 154(b) by 0 days.

(21) Appl. No.: 17/891,781

(22) Filed: Aug. 19, 2022

Related U.S. Application Data

(60) Provisional application No. 63/260,440, filed on Aug. 19, 2021.

(51) Int. Cl.
| | | |
|---|---|---|
| *A61B 5/00* | (2006.01) | |
| *G16H 40/67* | (2018.01) | |
| *A61B 5/11* | (2006.01) | |
| *G08B 21/04* | (2006.01) | |

(52) U.S. Cl.
CPC .......... *A61B 5/0022* (2013.01); *A61B 5/1112* (2013.01); *A61B 5/681* (2013.01); *A61B 5/746* (2013.01); *G08B 21/0453* (2013.01); *G16H 40/67* (2018.01)

(58) Field of Classification Search
CPC ..... A61B 5/0022; A61B 5/1112; A61B 5/681; A61B 5/746; G08B 21/0453; G16H 40/67
USPC .......................................................... 705/2
See application file for complete search history.

(56) References Cited

U.S. PATENT DOCUMENTS

| | | | | |
|---|---|---|---|---|
| 8,725,148 | B2 * | 5/2014 | George | H04L 65/1104 455/552.1 |
| 11,348,681 | B1 * | 5/2022 | Morrow | A61B 5/0022 |
| 2015/0154370 | A1 * | 6/2015 | Skaaksrud | H04L 67/303 705/2 |

(Continued)

FOREIGN PATENT DOCUMENTS

AU          2016200158 A1 *  8/2016

*Primary Examiner* — Omar Casillashernandez
(74) *Attorney, Agent, or Firm* — Perkins Coie LLP

(57) ABSTRACT

Systems and methods for aiding, supplementing, and/or increasing the monitoring capabilities of responsible persons over a supervised person are disclosed herein. In some implementations, the system includes one or more controlling persons, one or more supervising persons, a supervised person, and a cloud server. Each of the controlling persons and the supervising persons can have a personal electronic device. The supervised person can have a wearable electronic device. The electronic devices allow the controlling persons and the supervising persons to actively communicate with the cloud server to upload data related to the supervised person that is accessibly stored in the cloud server. In turn, the wearable device can include one or more sensors to measure and communicate various bioindicators to the cloud server. The system allows the controlling persons to monitor the health of, development of, and/or current control over the supervised person.

20 Claims, 25 Drawing Sheets

(56) References Cited

U.S. PATENT DOCUMENTS

2016/0147974 A1\* 5/2016 Sha ..................... G16H 10/20
705/2

\* cited by examiner

WEARABLE DEVICE FOR MONITORING THE HEALTH AND SUPERVISION OF A SUPERVISED PERSON AND RELATED SYSTEMS AND METHODS

CROSS-REFERENCE TO RELATED APPLICATIONS

The present application claims the benefit of U.S. Provisional Patent Application No. 63/260,440 filed Aug. 19, 2021, the entirety of which is incorporated herein by reference.

TECHNICAL FIELD

The present disclosure is generally related to systems and methods for supervising one or more persons. In particular, the present technology relates to wearable devices and related systems for monitoring the health and control over the supervised persons.

BACKGROUND

The health and safety of our loved ones is an invaluable aspect of daily life. We closely supervise our children's development through their early years and continue to supervise and care for them as they grow older. Then, as our parents and other family members age, we become increasingly reinvolved in their daily lives, care, and wellbeing. For many of us, the supervision of our children, elderly family members, and other loved ones requires the assistance of caregivers to balance the supervision required with busy work schedules and daily life. For example, American families spend upwards of forty billion dollars on childcare in a typical year, with more than half of American families with a child under the age of five paying for some amount of childcare. However, existing systems for monitoring who exactly is supervising our loved ones; whether the supervised person is happy, healthy, and exercised; and/or whether they experienced a significant event (such as a bad fall) while with a caregiver are outdated. For example, caregivers often cannot adequately report to parents whether each child under their supervision experienced anything noteworthy each day, while those daily experiences can have formative impacts on the child's development. Meanwhile, the young child (e.g., infant/toddler) may be incapable of adequately reporting on their daily experiences themselves, especially with respect to their physical, emotional, and mental development. Similarly, it is difficult to understand which caregivers best provide an environment for physical, emotional, cognitive, and/or social development (or maintaining development) to the people under their supervision even when we receive complete information. Further, it is even more difficult to understand how parents, legal guardians, caregivers, and other supervising persons can change their behaviors to help avoid and/or correct underdevelopment and/or deterioration.

Figure 1:
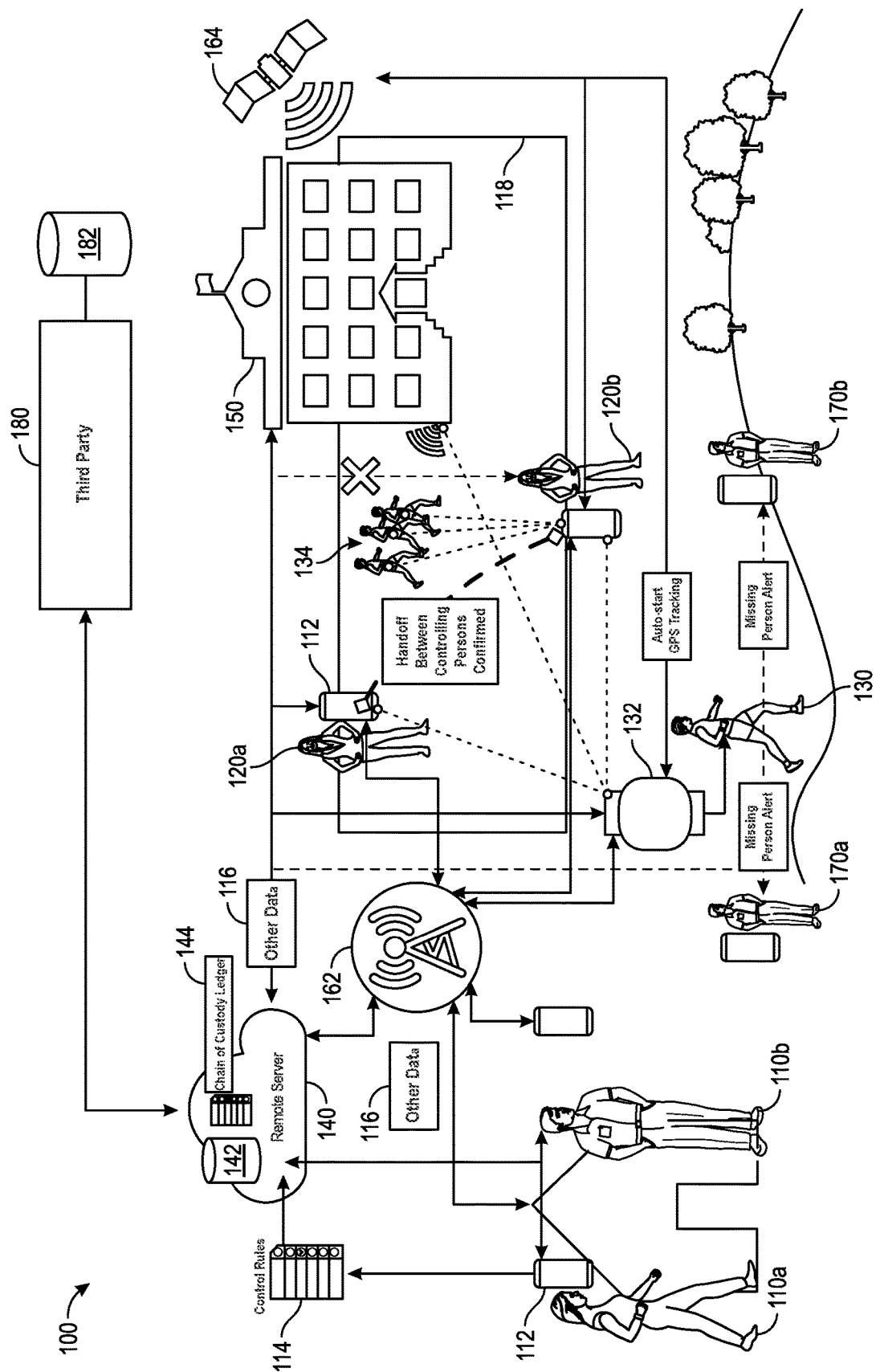
FIG. 1 is a schematic view of a system for monitoring a supervised person in accordance with some implementations of the present technology.

The drawings have not necessarily been drawn to scale. Similarly, some components and/or operations can be separated into different blocks or combined into a single block for the purpose of the discussion of some of the implementations of the present technology. Moreover, while the technology is amenable to various modifications and alternative forms, specific implementations have been shown by way of example in the drawings and are described in detail below. The intention, however, is not to limit the technology to the particular implementations described.

DETAILED DESCRIPTION

Overview

Systems and methods for aiding, supplementing, and/or increasing the monitoring capabilities of responsible persons over a supervised person are disclosed herein. In some implementations, the system includes one or more controlling persons (e.g., parents, guardians, and the like), one or more supervising persons (e.g., childcare workers), one or more supervised persons (e.g., a toddler), and a cloud server (or other remote servers) in communication with each of the controlling persons, the supervising persons, and the supervised person. For example, each of the controlling persons and the supervising persons can have a personal electronic device (e.g., a smartphone, tablet, personal computer, personal assistant, wearable device, and the like); while the supervised person can have a wearable electronic device. The electronic devices allow the controlling persons and the supervising persons (sometimes referred to collectively herein as "responsible persons") to actively communicate with one or more cloud servers to upload data related to the supervised person (e.g., medical history data, allergies, photos/videos, activity data, sleep data, data related to the current control over the supervised person (e.g., responsibility for the care and/or supervision of the supervised person), comments and instructions about care or instructions for the day (e.g., food preferences, supervisory care preferences), a specification of a daily routine, approved visitors for the supervised person, approved persons to pick up the supervised person, approved medications, approved dosages of medications, and the like) that is accessibly stored in the cloud server. In some implementations, the data is uploaded with a required security and/or permission level included. For example, medical data can be uploaded and be limited to viewers with a preset connection security level and/or a preset permissions level (e.g., allowing a parent to share medical data about their child with only a head childcare provider). Additionally, or alternatively, who can upload specific types of data can be limited by security and/or permission levels. For example, the permission levels can limit which controlling persons can upload information about supervision preferences.

Meanwhile, the wearable device can include one or more sensors that measure bioindicators of the supervised person (e.g., heart rate, skin temperature, skin conductivity, movement, heart-rate variability, resting heart rate, sweat chemical composition, hydration levels, nervous system electrical signals, stress levels, air quality, UV exposure, environmental chemical exposures, environmental chemical sensitivity, blood oxygen and/or pulse oxygen, voice commands and/or other sounds, electrical activity of the heart, atmospheric pressure, pressure on the wearable device, orientation of the wearable device on the supervised person, strength and direction of electromagnetic fields around the supervised person, and the like) and one or more communication components to communicate the bioindicators to the controlling persons and/or the supervising persons and/or directly to the cloud server(s). Once communicated out from the wearable device, the bioindicators can be accessibly stored in the cloud server(s).

As a result of the interconnection and data storage, for example, the system allows parents to quickly communicate with the cloud server to check the health and/or mental status of their toddler, monitor the location of their toddler, define rules for the supervision of their toddler, check to ensure the rules for the supervision of their toddler are followed by the childcare providers, and/or review a chain of custody for their toddler in a given day. Accordingly, the system can provide parents with some peace of mind regarding the status of their toddler and/or allow parents to make more informed decisions about the childcare workers they entrust with the supervision of their toddlers.

In a specific, non-limiting, example, the system can include two parents, a daycare service with multiple childcare providers, and one or more toddlers equipped with wearable devices. The parents can access the cloud server to set control rules for their toddler (mandatory rules, and/or suggested rules) to be followed by the daycare service, such as rules on where the toddler can be taken without additional permission, nutritional rules for any snacks provided by the daycare service, and rules on who can (and cannot) be left in control over of the toddler (e.g., trusted with supervision the toddler). The daycare service can then access the cloud server to review the rules, request any changes, and implement the control rules when in supervising of the toddler. Within this example system, the parents and daycare service can also follow a handoff procedure to update a chain of custody ledger with the cloud server. For example, when a first parent drops the child off at the daycare, the handoff can be reflected in the chain of custody ledger, allowing a second parent to see the updated supervision over the toddler. Further, when one of the childcare workers takes over for another, the shift in supervision can also be reflected in the chain of custody ledger, allowing the parents to quickly review who is currently supervising the toddler throughout the day.

Additionally, or alternatively, the wearable device on the toddler can communicate updates on the physical, mental, and/or emotional status of the toddler throughout the day and/or the toddler's location. To do so, the wearable device can communicate with an electronic device of any nearby responsible person (e.g., the electronic device of the childcare workers), a nearby beacon, one or more internet of things (IoT) devices in its vicinity, and/or directly to the cloud server (e.g., over an internet or cellular connection). The status updates can allow the toddler's parents to easily monitor the health and development of their child throughout the day, as well as the child's physical location. Further, the status updates can be timestamped, allowing the toddler's parents (and/or the system) to cross-reference significant events with which the childcare worker was supervising their toddler at the time. As a result, the parents can request additional information from that childcare worker, determine which childcare workers should (or should not) be trusted with the supervision of the toddler, and/or determine which childcare workers should (or should not) the toddler should spend time with. For example, a record indicating that the toddler was especially happy and/or mentally stimulated while under the supervision of a particular childcare worker can indicate that the toddler should spend additional time with that particular childcare worker. In an alternative example, a record indicating that the toddler was especially unhappy or experienced a significant event that is unaccounted for while under the supervision of a particular childcare worker may indicate that the particular childcare worker should not be trusted with the toddler.

In some implementations of the present technology, the cloud server (or other remote servers) includes one or more components that automatically review the data (including data from the responsible persons and/or the wearable sensor) related to the supervised person. In doing so, the cloud server can generate a report on the physical, mental, and/or emotional health and/or development of the supervised person. For example, the cloud server can indicate when a toddler may be getting sick, may not have had enough sleep, etc. Additionally, or alternatively, the cloud server can generate recommendations to the responsible persons related to the physical, mental, and/or emotional health and/or development of the supervised person. For example, the cloud server can recommend additional cognitive activities to generate additional mental stimulation and development when detecting that a toddler has fallen behind predetermined milestones (e.g., the CDC-defined milestones for child development).

For ease of reference, components of the system are sometimes described herein with reference to top and bottom, upper and lower, upwards and downwards, and/or horizontal plane, x-y plane, vertical, or z-direction relative to the spatial orientation of the implementations shown in the figures. It is to be understood, however, that the components can be moved to, and used in, different spatial orientations without changing the structure and/or function of the disclosed implementations of the present technology.

Further, although primarily discussed herein as a system for use to supervise a toddler, one of skill in the art will understand that the scope of the technology is not so limited. For example, the systems and methods disclosed herein can also be used to aid and/or supplement the supervision of a baby, a child, an elderly person, a differently-abled person, and/or any other person that requires at least partial supervision over their daily activities. Accordingly, the scope of the technology is not confined to any subset of implementations described herein.

Systems of the Present Technology

FIG. 1 is a schematic view of a system 100 for monitoring a supervised person 130 in accordance with some implementations of the present technology. The system 100 interconnects one or more controlling persons with one or more supervising persons to share the supervision of a supervised person 130 (e.g., a baby, toddler, child, elderly person, differently-abled person, and/or any other person requiring supervision). The illustrated implementation includes two controlling persons 110, referred to individually as a "first controlling person 110a" and a "second controlling person 110b." In various implementations, the first and second controlling persons 110a, 110b can be a first parent, godparent, grandparent, older sibling, any legal guardian, an adult providing care to an elderly family member, an adult providing care to another elderly person, and/or any other suitable person that exercises a degree of control over the supervised person's daily activities and/or overall well-being. Further, in various implementations, the system 100 can include fewer, or additional, controlling persons 110. For example, the system 100 can include two parents and an older sibling; a single parent; or multiple siblings that share caregiving responsibilities for an elderly parent.

The illustrated implementation also includes one or more supervising persons 120 (two shown, referred to individually as a "first supervising person 120a" and a "second supervising person 120b"). In various implementations, the first and second supervising persons 120a, 120b can be various caregivers (e.g., a child care worker (such as a daycare worker, nursery worker, nanny, or babysitter), a family caregiver, a home health caregiver, an assisted living nurse or any other nursing practitioner, and the like), a preschool or elementary school teacher, various other school officials, and/or any other suitable person responsible for the supervised person 130. Further, in the illustrated implementation, the supervising persons 120 are also responsible for one or more additional supervised persons 134. For example, when the supervising persons 120 are a part of a daycare provider, the additional supervised persons 134 can be the other toddlers and/or children entrusted to the daycare.

As further illustrated in FIG. 1, the system 100 connects each of the controlling persons 110 and the supervising persons 120 (e.g., the responsible persons) to a remote server 140 (e.g., a cloud server and/or any other suitable remote server). In the illustrated implementation, each of the responsible persons is interconnected to the system 100 through one or more electronic devices 112 (e.g., a smartphone, tablet, personal computer, personal assistant, wearable device, IoT device, AR/VR device, and the like). For example, each of the electronic devices 112 can communicate via shortrange wireless components (e.g., Bluetooth® components and the like), internet communication components that connect to a wireless or wired network (e.g., the internet), and/or cellular components that connect to a cellular network 162. The communication can help the responsible persons maintain a record of the control over of the supervised person 130 within the system; coordinate regarding basic needs for the supervised person 130; coordinate regarding physical, mental, and/or an emotional status of the supervised person 130; and/or communicate any other suitable information. The actions of the responsible persons in the system 100 can be performed through one or more user interfaces and/or modules on the electronic devices 112. Accordingly, one of skill in the art will understand that, as used herein, the actions of the responsible persons with respect to the system 100 can be performed through the electronic devices 112 (e.g., through various subsystems 300, 400 thereon, discussed in more detail below), unless otherwise indicated.

For example, the controlling persons 110 can upload, edit, and/or update a set of control rules 114 that are stored within the remote server 140, and the control rules 114 can then be accessed by a supervising person 120 to ensure appropriate supervision of the supervised person 130. In various implementations, the control rules 114 include rules for how much supervision must be given to the supervised person 130 (e.g., constant supervision, whether semi-supervised playtime is allowed, and the like); who is permitted to supervise the supervised person 130 (e.g., when supervision must be maintained by a particular caregiver or set of caregivers rather than handed off); what activities the supervised person 130 can engage in such as types of play, field trips, sports, movie and television watching controls, and the like; what activities the supervised person 130 must engage in such as a daily nap, daily exercise, learning activities, and the like; a preferred and/or required schedule and/or routine for the supervised person 130; what foods the supervised person 130 can consume and/or cannot consume; a predefined geographic location for the supervision of the supervised person 130; geographical limits to field trips, errands, and/or any other deviations from where the supervised person is dropped off; rules for proscribed medical care, such as a preferred hospital, pediatrician, authorized medications (e.g., Advil®, Tylenol®, and the like and/or authorized dosages of medications; authorized visitors for the supervised person 130; authorized persons to receive the supervised person 130 (e.g., a parent can specific that a grandparent, godparent, and/or older sibling can pick up their child from daycare); and/or various other suitable rules related to the supervision of the supervised person 130. In some implementations, the system 100 includes tiers of control between the first and second controlling persons 110a, 110b. For example, the first controlling person 110a can have more power in setting and/or adjusting the control rules 114 than the second controlling person 110b (e.g., allowing parents to exercise more control than an older sibling).

The control rules 114 can also include information related to the supervision of the supervised person 130, such as known allergies, known medical conditions, medical history information, known behavioral patterns, recent developments or updates, and/or various other data that impacts the supervision of the supervised person 130. Non-limiting examples of medical history information can include information on vaccinations, family medical history, diagnoses specific to the supervised person, past medical events such as surgeries, illnesses, and/or major medical events (e.g., seizures). Non-limiting examples of recent developments or updates include recent diagnoses, broken bones and/or other physical trauma, recently experienced mental and/or emotional trauma such as the loss of a family member, cognitive and/or behavioral developments such as learning to use the restroom for toddlers and loss of memory in adults, and the like.

Additionally, or alternatively, each of the responsible persons can upload, edit, update, and/or review developmental data related to the supervised person 130, such as data about their daily activities, evaluations of interactions with the supervised person, evaluations of their developmental status, achieved milestones, and the like. For example, each of the responsible persons can upload data related to the daily activities of the supervised person 130 such as reports on physical and/or cognitive exercise, estimated sleep during naps and/or overnight, nutritional intakes, eating and/or sleeping patterns (e.g., when the supervised person 130 tends to nap and/or be hungry), an assessment of various cognitive elements (e.g., ability to learn, participate in class, attention span, memory, comprehension of text, and the like) a mood of supervised person, reports on injuries and/or stress events, reports on medication administrated to the supervised person, and/or any other suitable information about the daily activities of the supervised person 130.

Additionally, or alternatively, as the responsible persons complete actions and/or communicate through the system 100, their actions and/or communications can be routed through and/or relayed to the remote server 140. Further, as illustrated in FIG. 1, the remote server 140 includes one or more databases 142 (one shown) that can store a record of the control rules 114, various communications between the responsible persons, developmental data contained in communications, other data related to the supervised person 130 (e.g., medical history data, allergies, background data, food preferences and/or permissions, supervisory care instructions, and the like), a record of the control over the supervised person 130 (e.g., responsibility for providing care to and/or supervising the supervised person 130), and/or any other suitable information. Further, in some implementations, the remote server 140 maintains a secure ledger with any of the information discussed above. For example, in the illustrated implementation, a record of any handoffs can be recorded in a chain of custody ledger 144 ("ledger 144") that is stored on and accessed through the remote server 140. The ledger 144 can maintain a complete record of who was responsible for the supervised person 130 throughout a day in a secure, unalterable manner. Accordingly, for example, the ledger 144 allows a parent to review the supervision of their toddler when the toddler indicates that they had a particularly good or bad day. Additional details on the handoff functions of the system 100 are discussed below, especially in reference to FIG. 5.

As further illustrated in FIG. 1, the responsible persons can communicate with the remote server 140 to create, edit, receive, and/or download other data 116. The other data 116 communicated to the remote server 140 include pictures/videos/audios of the supervised person 130, reports on events related to the supervised person 130, reviews of supervising persons 120, other information related to the supervision of the supervised person 130, indications of deviations from a daily routine (e.g., that the supervised person 130 missed a nap or had some additional meal), and/or other information related to the daily activities of the supervised person 130. In some implementations, the other data 116 can also be supplemented by reports from a wearable device 132 on the supervised person 130.

In the illustrated implementation, the wearable device 132 can communicate data to the electronic devices 112 and/or directly the remote server 140 through any suitable network connection. To do so, as described in more detail below, the wearable device 132 can include a shortrange wireless communication component, an internet communication component, and/or a cellular component. Further, to collect the data, the wearable device 132 can include one or more sensors that collect bioindicator data that helps monitor the health and mental status of the supervised person 130, such as skin temperature sensors, photoplethysmogram (PPG) sensors, accelerometers, skin conductivity sensors, heart-rate variability sensors, resting heart rate sensors, sweat chemical composition sensors, nervous system electrical sensors, air quality sensors, UV exposure sensors, sensors to detect environmental chemicals, blood oxygen and/or pulse oxygen sensors, voice recognition, electrocardiogram (ECG) sensor, pressure sensors, gyroscopes, magnetometers, and the like. The bioindicator data from the sensors can be continuously and/or periodically communicated throughout the system 100. For example, the wearable device 132 can communicate updates to the electronic device 112 of any responsible person whenever their electronic devices 112 are within range of the shortrange wireless communication component; to the remote server 140 through the internet when a wireless connection is available; and/or to the remote server 140 through the cellular network 162 whenever the shortrange and internet options are unavailable. The bioindicator data from the sensors can then be relayed to the controlling persons 110 so they can monitor the physical, emotional, and/or mental condition of the supervised person 130. The bioindicator data from the sensors can also be processed and/or mined by one or more modules on the remote server 140 to assist the controlling persons 110 with monitoring the physical, emotional, and/or mental condition of the supervised person 130.

For example, the cloud server 140 can use the developmental data and the bioindicator data (referred to collectively as "target data") to generate one or more predictive models specific to a particular supervised person 130 and/or applicable to supervised persons overall. The predictive models can be used to evaluate target data identify a current physical, emotional, cognitive, and/or social developmental status (also referred to collectively herein as the "developmental status") for a supervised person, predict the impact various changes will have on the developmental status for the supervised person, and/or generate recommendations for changes to intentionally impact the developmental status for the supervised person in a desired way.

The specific predictive models can also be customized to a specific supervised person, for example, by accounting for their typical reactions to changes (e.g., whether they are more or less sensitive to changes) to more accurately identify how activities and/or actions will impact the developmental status of the particular supervised person. The general predictive models can be used to help identify broad trends in the impact of various activities and/or actions on the developmental status of supervised persons (e.g., to assess how various levels of exercise generally impact the developmental status of toddlers), to identify previously unrecognized correlations that may indicate some causal relation, and/or to make broad recommendations for activities and/or actions to intentionally impact the developmental status of supervised persons. Further, the general predictive models can be used to assess the developmental status of a new supervised person in the system given a small amount of target data on the new supervised person.

In some implementations, the wearable device 132 can process the bioindicator data, before sending the update related to the bioindicator data, to better monitor the physical, emotional, and/or mental condition of the supervised person 130. For example, the wearable device 132 can process the bioindicator data to detect emotional, cognitive, and/or physical developments and/or events (e.g., a high-stress event) and send the update in response to the detected event.

The wearable device 132 can also include a global positioning system (GPS) component that communicates with one or more GPS satellites 164 to track the location and/or movement of the supervised person 130. The GPS component allows one or more responsible persons to define a geofence boundary 118 to aid in monitoring the supervised person 130. For example, the geofence boundary 118 can surround the perimeter of a playground associated with a daycare or school. If the supervised person 130 exits the geofence boundary 118 without a suitable explanation, the system 100 can send an alert to any of the responsible persons. Additional details on the geofencing aspects of the system 100 are discussed below, especially in reference to FIG. 6.

In some implementations, one or more of the additional supervised persons 134 are also wearing a wearable device 132, connecting them to the supervising persons 120 and their own respective controlling person(s) (not shown). In some implementations, the geofencing features discussed above can be implemented broadly for each of the supervised persons 130, 134. For example, the supervising persons 120 can define the geofence boundary 118 as broadly applying to each of the supervised persons 130, 134 at a single time (e.g., while children are at recess), such that if any of the supervised persons 130, 134 break the geofence boundary the supervising persons 120 are alerted. Similarly, in some implementations, one or more control rules 114 are be set for each of the supervised persons 130, 134 broadly.

In the implementation illustrated in FIG. 1, the supervising persons 120 are members of an associated caregiving facility 150, such as a contracting school, daycare or other childcare facilities, assisted living facility, nursing center, and/or any other suitable entity. In some implementations, the caregiving facility 150 includes features that assist communication throughout the system 100 (e.g., various IoT-enabled devices, beacons, WiFi hotspots, sensors, and the like) dispersed throughout the caregiving facility 150. Further, in some implementations, the caregiving facility 150 includes a set of supervising persons 120 that have an organizational hierarchy and/or sub-divisions for supervising groups of one or more supervised persons 130.

For example, the first supervising person 120a can define control rules 114 applying to the supervised persons 130, 134 that the second supervising person 120b can review and follow. In some implementations, the control rules 114 defined by the first supervising person 120a must be within a tolerance of the control rules 114 defined for each of the supervised persons 130, 134 individually (e.g., by their respective controlling persons). To provide a specific example, the controlling persons of each of the supervised persons 130, 134 may indicate that the supervised persons 130, 134 are not to leave a specific facility (e.g., a daycare facility) without their permission. In turn, the first supervising person 120a can indicate that the second supervising person 120b cannot remove the supervised persons 130, 134 from a specific room within the facility without the permission of the first supervising person 120a.

As further illustrated in FIG. 1, the system 100 can also connect with one or more third parties 160 (one shown), each having its own database 162 to store information related to the developmental status of the supervised person 130 and/or the additional supervised persons 134. In some implementations, the remote server 140 can share some, or all, of the target data with the third parties 180. The third parties 160 can then study the target data to, for example, identify general trends in development for supervised persons based on their experiences, bioindicators, and/or daily routines. Additionally, or alternatively, the third parties 160 can mine the target data to generate predictive models (both specific and general) for supervised persons. Once generated, the third parties 160 can communicate the predictive models back to the cloud server 140, which can then use the predictive models in one or more modules accessible by the responsible persons. Like the predictive models generated by the cloud server 140, the predictive models generated by the third parties 160 can be used to identify a current developmental status of the supervised person 130 (or any of the additional supervised persons 134); predict how various changes will impact the developmental status of the supervised person 130; and/or make recommendations for changes to intentionally impact the developmental status of the supervised person 130.

By collecting and linking bioindicator data with data from the supervised persons, as well as collecting the target data in bulk, the system 100 is expected to greatly improve the accuracy of predictive models used to assess the current developmental status of supervised persons and make decisions about changes to the supervised persons' lives. For example, by closely monitoring the bioindicators of a child alongside assessments of the child, the system 100 is expected to generate more accurate predictive models for physical, emotional, cognitive, and/or social development in children. In another example, by closely monitoring the bioindicators of an elderly person alongside assessments of the elderly person, the system 100 is expected to generate more accurate predictive models that allow for early detection of various illnesses that cause a decline and/or early intervention against the illnesses. Further, the system 100 is expected to provide a non-invasive point of entry for academic research into human development, together with checks that help ensure the data from the system is accurate (e.g., checks between evaluations of the supervised person and their bioindicator data).

As further illustrated in FIG. 1, the system 100 can also include a connection to one or more additional persons 170 (two shown, labeled 170a and 170b). The additional persons 170 can be alerted by a variety of functions in the system to search for the supervised person 130, check on the supervised person 130, rescue the supervised person 130, and the like. Purely by way of example, when the supervised person 130 breaches a geofence boundary, the responsible persons can be alerted to the breach. Any of the responsible persons can then instruct the system 100 to notify additional persons 170 that the supervised person 130 needs to be located. In various specific, non-limiting examples, the additional persons 170 can be emergency responders (e.g., security officers, police officers, fire departments, neighborhood watch, and the like), other parents or guardians on the system 100, other supervising persons on the system 100, and the like. The notification of the additional persons 170 can help locate the supervising person 130 quickly to resolve the breach. In another example, when the supervised person 130 presses a panic button on the wearable device 132, the system 100 can respond by alerting the additional persons 170 to check on and/or rescue the supervised person 130. In yet another example, when the bioindicator data for a supervised person 130 indicate prolonged and/or recurring periods of stress, the system 100 can alert additional persons 170 (e.g., child services) to check on the supervised person 130.

Figure 2:
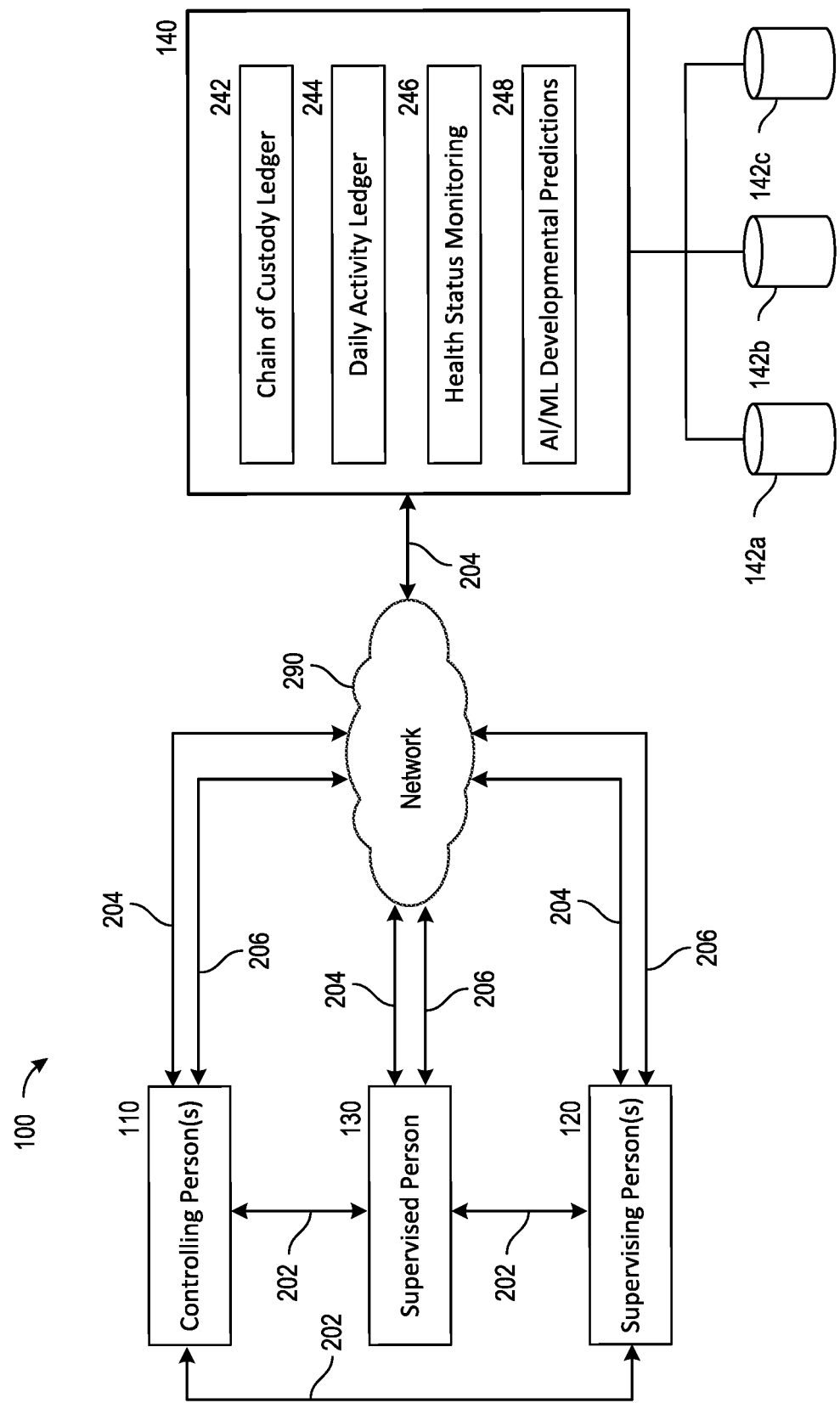
FIG. 2 is a network diagram of the system for monitoring a supervised person in accordance with some implementations of the present technology.

FIG. 2 is a network diagram of the system 100 for monitoring the supervised person 130 in accordance with some implementations of the present technology. As illustrated in FIG. 2, each of the controlling persons 110, the supervising persons 120, and the supervised person 130 can have shortrange communication channels 202 therebetween. As discussed above, the shortrange communication channels 202 can be established over any suitable shortrange wireless standard (e.g., Bluetooth®, Zigbee®, Z-Wave®, Wi-Fi HaLow®, or any other suitable shortrange standard). The shortrange communication channels 202 allow the controlling persons 110, the supervising persons 120, and the supervised person 130 to communicate locally via a relatively low-energy, secure standard. However, the controlling persons 110, the supervising persons 120, and the supervised person 130 are not always within range of each to establish the shortrange communication channels 202. Accordingly, as further illustrated in FIG. 2, each of the controlling persons 110, the supervising persons 120, and the supervised person 130 can also communicate with a network 290 (e.g., an internet network, a cellular network, and so on). To do so, each of the controlling persons 110, the supervising persons 120, and the supervised person 130 can establish an internet communication channel 204 (e.g., a WNIC connecting to WiFi) and/or a cellular communication channel 206.

As further illustrated in FIG. 2, the network 290 is connected to the remote server 140 through an internet communication channel 204. Accordingly, the remote server 140 can communicate with each of the controlling persons 110, the supervising persons 120, and the supervised person 130 over the network, for example to receive data, control rules, and/or facilitate any of the supervisory monitoring actions discussed above (e.g., to activate a geofence boundary). In the illustrated implementation, the remote server 140 includes three databases 142a-142c to store the data, control rules, and/or any relevant communications. For example, in the illustrated implementation, the remote server 140 includes four modules (referred to individually as first-fourth modules 242-248) that can be stored in the databases 142a-142c and executed in response to various activities in the system 100 (e.g., in response to a request from a controlling person 110).

In the first module 242, the remote server 140 maintains a chain of custody ledger that reflects the control over the supervised person. When one responsible person hands-off control (e.g., responsibility for the supervised person) to another responsible person, the change in control over the supervised person is reflected in the chain of custody ledger. For example, when a first parent drops their toddler off for daycare, the parent and the daycare can execute a handoff that is recorded in the chain of custody ledger. Any responsible party (e.g., a second parent) with access to the chain of custody ledger can then see that the daycare is responsible for the toddler. Later, the second parent can pick-up the toddler from daycare and execute another handoff while doing so, and the change in control over the supervised person is reflected in the chain of custody ledger. Afterwards, the first parent can view the change in control through the chain of custody ledger to, for example, confirm the second parent picked-up the toddler. In another example, the chain of custody ledger can be specific to the daycare worker, thereby allowing either of the parents to review which daycare worker is currently responsible for the toddler. The specificity of the chain of custody ledger can, for example, allow the parents to determine which daycare worker was responsible for a toddler when the toddler expresses they had a particularly good or bad day; allows the parents to more quickly locate their child in an emergency; and/or allows the parents to ensure control rules are being followed by the daycare.

In some implementations, the first module 242 includes a process for alerting responsible persons when the chain of custody is broken by an indication that the supervised person 130 is too far away from the person indicated to be currently responsible. In various implementations, the range indicating the chain of custody is broken can be set by the distance for shortrange communications between the supervised person 130 and the responsible person, whether the supervised person 130 and the responsible person are connected to the same network (e.g., connected to the same WiFi), whether the supervised person 130 is still present within a set geofence boundary, a predetermined distance measured using a GPS location of each of the supervised person 130 and the responsible person, and/or any other suitable metric. In some implementations, the first module 242 can include a time-out feature that requires the chain of custody to be broken for more than a predetermined period of time before taking any further action. The predetermined time can be 30 seconds, 60 seconds, 2 minutes, 5 minutes, or any other suitable period. The time out function allows, for example, the responsible person to use the restroom without triggering a break in the chain of custody. Once the chain of custody is broken, the first module 242 can begin recording the GPS location and/or cellular connection of the supervised person 130 and alert the last responsible person in the record of the chain of custody. In some implementations, the first module 242 also alerts the controlling person(s) 110 each time the chain of custody is broken. In some implementations, the first module 242 provides time for an explanation from the last responsible person before alerting the controlling person(s) 110 (e.g., that a handoff occurred and was not properly recorded), record any explanation for later review by the controlling person(s) 110, and/or alert the controlling person(s) 110 after a predetermined amount of time if no explanation is received. In some implementations, the first module 242 also alerts one or more additional persons (e.g., other supervising persons associated with the supervised person 130, other supervising persons and/or controlling persons connected to the network 290 (e.g., other parents) and/or in the vicinity of the supervised person 130, and/or emergency services).

The first module 242 can include a process for alerting responsible persons when the chain of custody is broken by an unrecorded handoff. Purely by way of example, an unrecorded handoff can occur when a controlling person 110 (e.g., a parent) picks up the supervised person 130 (e.g., a toddler) without properly executing the handoff process (e.g., picks up the toddler in a rush). The remote server 140 can detect the break in the chain of custody, for example, when updates from the supervised person 130 are received from a new responsible person (e.g., the controlling person 110) and not the currently responsible person (e.g., the supervising person 120), indicating a shift in who is in the vicinity of the supervised person 130. Once the break in the chain of custody is detected, the first module 242 can include a process for rectifying the chain of custody. Purely by way of example, the first module 242 can require a controlling person 130 with a predetermined level of authorization (e.g., separating parents from older siblings) to approve the currently responsible person and execute a handoff to the currently responsible person on the backend.

In the second module 244, the remote server 140 maintains a record of the daily activity of the supervised person. The record can be updated with data from any of the responsible persons. For example, a parent can update the record of the daily activity to indicate that the supervised person did not sleep well the night before and has been ornery in the morning to help explain poor behavior to other responsible persons. Additionally, or alternatively, the record can be updated with data from the wearable device 132 (FIG. 1), such as bioindicators from the one or more onboard sensors. Accordingly, the record can include an indication of how much exercise the supervised person 130 got during a day, their general health throughout the day, and/or their mood throughout the day. The record can then be accessed by one or more responsible persons (e.g., the controlling persons 110) to monitor the daily physical, mental, and emotional activity of the supervised person 130. Additionally, or alternatively, the record can be accessed by one or more other modules in the remote server 140 to automatically monitor the physical, mental, and emotional activity of supervised person 130.

For example, in the third module 246, the remote server 140 can automatically monitor the health of the supervised person 130 using the record of the daily activity. For example, the remote server 140 can determine when the bioindicators suggest that the supervised person 130 is sick, is overexercised for a period (e.g., a day, week, month, or any other suitable period), is under exercised in the period, has not gotten an appropriate amount of sleep, has experienced a significant mental or emotional event, and the like. Once detected, the remote server 140 can notify the relevant responsible persons of the detected event. In some implementations, the remote server 140 can determine a current medical status of the supervised person 130 from the bioindicators, including when they are healthy and/or have completely normal bioindicators, and make the medical status available to any of the responsible persons. The continuous medical status can provide some piece of mind to the responsible persons regarding the health of the supervised person 130, can help a responsible person make determinations on supervising activities (e.g., whether the supervised person 130 needs an additional nap or additional exercise), and/or can help a responsible person detect a deviation before it happens (e.g., detecting a cold early on). In some implementations, the third module 246 includes predetermined and/or preset alerts that send a notification to a responsible person when a specific health-related event is detected. For example, the controlling persons 110 can be notified when a significant emotional and/or mental event is indicated by the bioindicators, allowing the controlling persons 110 to adequately address the event with the supervised person 130.

In the fourth module 248, the remote server 140 can execute one or more artificial intelligence and/or machine learning (AI/ML) algorithms to review the physical, emotional, and/or mental development of the supervised person 130. For example, the AI/ML algorithms can use the data from the wearable device 132 (FIG. 1) to study the bioindicators for the supervised person 130, evaluate their physical, emotional, and/or mental development, and/or make recommendations to the responsible persons regarding the same. In some implementations, the recommendations include an indication that the supervised person 130 would benefit from additional exercise, additional social interaction, and/or to additional mental stimulation. Additionally, or alternatively, the recommendations can include updates to the nutritional intake of the supervised person 130, suggestions for maintaining better hydration of the supervised person 130, conforming naps and bedtimes to observed sleep patterns for the supervised person 130 decision support articles at important developmental milestones for the supervised person 130, an identification of recurring stressful events for the supervised person 130 and recommendations for addressing the stressful events and/or communicating with the supervised person 130 about the stressful events, and the like. In some implementations, the recommendations include articles on developmental related topics specific to the supervised person 130. For example, the AI/ML algorithms may determine that the supervised person 130 (e.g., a toddler) does not sleep well and recommend articles on improving the sleep of toddlers to the responsible persons.

Examples of the artificial intelligence algorithms include, but are not limited to, case-based reasoning, rule-based systems, artificial neural networks, decision trees, support vector machines, regression analysis, Bayesian networks (e.g., naïve Bayes classifiers), genetic algorithms, cellular automata, fuzzy logic systems, multi-agent systems, swarm intelligence, data mining, machine learning (e.g., supervised learning, unsupervised learning, reinforcement learning), and hybrid systems. Further various machine learning algorithms and techniques are suitable for use with the present technology. In some implementations, the machine learning model is initially trained on a training data set, which is a set of examples used to fit the parameters (e.g., weights of connections between "neurons" in artificial neural networks) of the model. For example, the training data set can include a number of suitable reference sets associated with other supervised persons (e.g., data associated with other toddlers) that are stored in one of the databases 142*a*-142*c*.

In some implementations, the machine learning model (e.g., a neural network or a naïve Bayes classifier) may be trained on the training data set using a supervised learning method (e.g., gradient descent or stochastic gradient descent). The training dataset can include pairs of generated "input vectors" with the associated corresponding "answer vector" (commonly denoted as the target). The current model is run with the training data set and produces a result, which is then compared with the target, for each input vector in the training data set. Based on the result of the comparison and the specific learning algorithm being used, the parameters of the model are adjusted. The model fitting can include both variable selection and parameter estimation. The fitted model can be used to predict the responses for the observations in a second data set called the validation data set. The validation data set can provide an unbiased evaluation of a model fit on the training data set while tuning the model parameters. Validation data sets can be used for regularization by early stopping, e.g., by stopping training when the error on the validation data set increases, as this may be a sign of overfitting to the training data set. In some implementations, the error of the validation data set error can fluctuate during training, such that ad-hoc rules may be used to decide when overfitting has truly begun. Finally, a test data set can be used to provide an unbiased evaluation of a final model fit on the training data set.

Example Systems and Methods Related to the Responsible Persons

Figure 3:
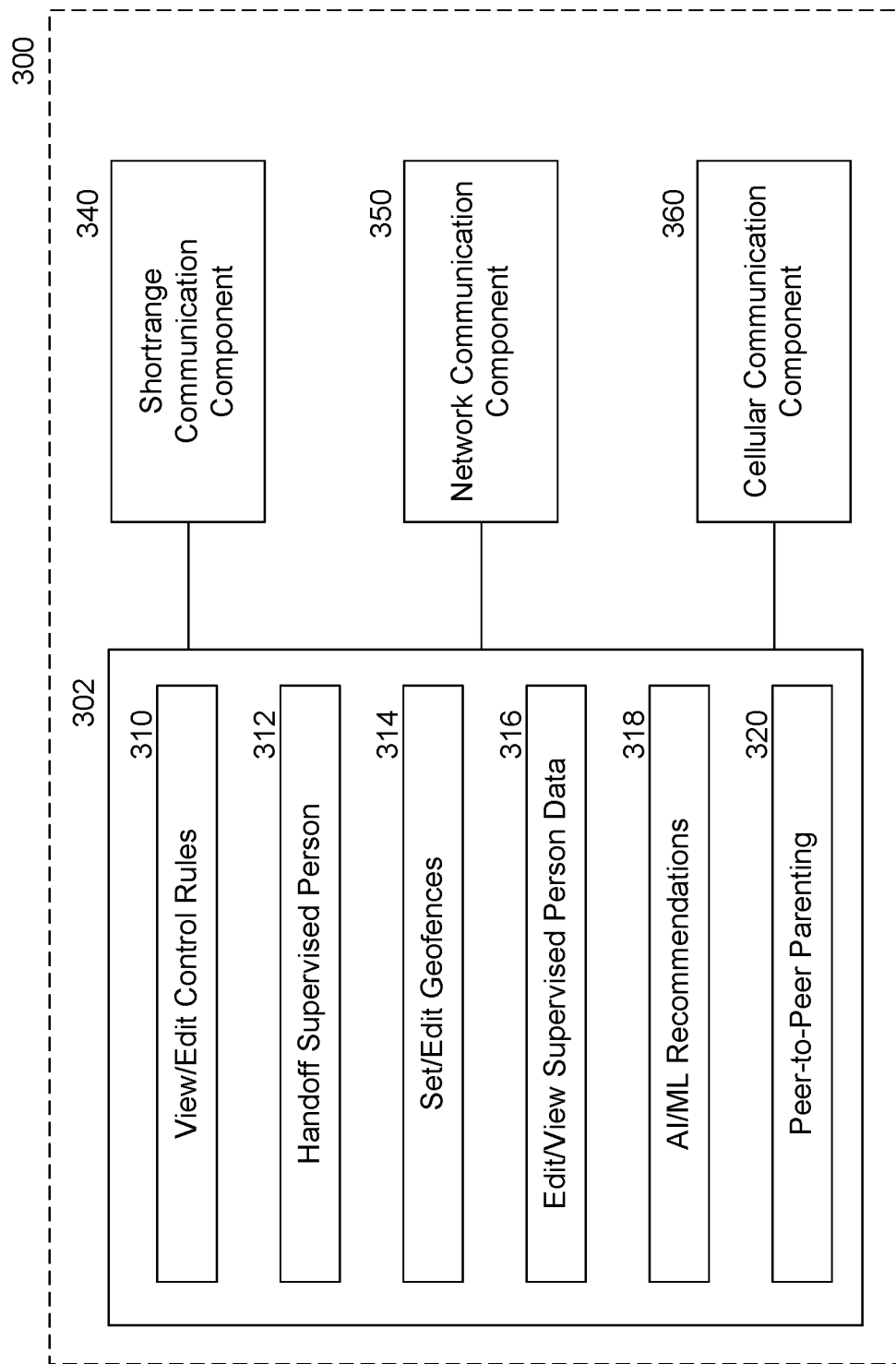
FIG. 3 is a schematic diagram of a platform for a controlling person in the system for monitoring a supervised person in accordance with some implementations of the present technology.

FIG. 3 is a schematic diagram of a subsystem 300 associated with a controlling person in a system for monitoring a supervised person in accordance with some implementations of the present technology. The subsystem 300 can be deployed in the electronic device 112 discussed above with respect to the system 100 of FIG. 1. A processor and/or a storage component are not illustrated in FIG. 3 to avoid obscuring the illustrated components of the subsystem 300. However, one of skill in the art will understand that the subsystem 300 can include one or more processors and any suitable number of storage components to facilitate operation of the subsystem 300 as described herein.

As illustrated in FIG. 3, the subsystem 300 includes an operating platform 302 ("platform 302") with one or more modules (six shown, referred to individually as first-sixth modules 310-320), a shortrange communication component 340, an internet communication component 350, and a cellular communication component 360. The shortrange communication component 340 can communicate over a shortrange wireless standard (e.g., a Bluetooth®, Zigbee®, Z-Wave®, Wi-Fi HaLow®, or any other suitable shortrange standard) to enable the subsystem 300 to communicate directly with other subsystems and devices that are within a local communication range. The internet communication component 350 enables the subsystem 300 to communicate with a network (e.g., the network 290 discussed above with respect to FIG. 2) over a wireless (or wired) internet connection (e.g., a WiFi connection or ethernet connection), allowing the subsystem 300 to connect with other subsystems and devices also connected to the network. Similarly, the cellular communication component 360 enables the subsystem 300 to communicate with the network through a cellular internet connection (e.g., based on a 3G, 4G, LTE, 5G, 6G, or other standard). The platform 302 is operably coupled to each of the shortrange communication component 340, the internet communication component 350, and the cellular communication component 360.

Accordingly, any of the modules in the platform 302 can communicate with other subsystems and devices locally and/or over the network. Various examples of the modules are discussed in more detail below.

In the first module 310, a controlling person can set, review, update, and/or edit the control rules related to the supervised person. In some implementations, the first module 310 includes a number of preset prompts for common control rules (e.g., required naptimes per day, nutritional rules, rules related to where the supervised person can be taken without additional permission, rules related to who can be responsible for the supervised person, and the like). The preset prompts can help a controlling person quickly set the control rules as well as help establish a common set of rule types for controlling persons and supervising persons to be aware of. The first module 310 can also include space for custom and/or non-prompted control rules to be entered. The custom and/or non-prompted control rules allow the control rules to be flexible to independent requests from the controlling person and/or the individual needs of the supervised person.

In the second module 312, the controlling person can handoff the control over the supervised person from a controlling person to (and from) a supervising person and/or another controlling person. Various examples of the process for handing off control are discussed in more detail below with respect to FIG. 5.

In the third module 314, the controlling person can set, edit, and/or remove geofence boundaries. In various implementations, the geofence boundaries can be set by drawing a perimeter on a map within a user interface on the subsystem 300, selecting one or more areas within a map with predefined boundaries (e.g., selecting a public park), selecting one or more saved geofence areas, placing and registering one or more waypoints and/or beacons that define the geofence boundary, and/or any other suitable mechanism. Once set, the geofence boundaries can help monitor the supervised person to ensure they remain within the geofence boundary. Various examples of the process for alerting the controlling person (and/or the supervising person) are discussed in more detail below with respect to FIG. 6. When the geofence boundary is no longer needed, the controlling person can then use the third module 314 to remove the geofence boundary.

In the fourth module 316, the controlling person can edit and/or view data related to the supervised person. For example, the fourth module 316 can allow the controlling person to review data from any of the sensors on the wearable device 132 (FIG. 1), as well as any information that the remote server 140 has generated and/or collected based on the sensor data (e.g., information related to estimated child development based on the sensor data). The fourth module 316 can also allow the controlling person to review data uploaded by any other controlling person and/or any of the supervising persons, such as information related to an event such as a breach of the geofence, an injury from an accident (e.g., indicating that the supervised person fell during a recess and received a scrape), a tantrum or other emotional event, and/or any other suitable event. The data uploaded by another controlling person and/or supervising person can also include medical updates. For example, if one of the responsible persons discovers an allergy, they can upload an update that is viewable in the fourth module 316. The data uploaded by another controlling person and/or supervising person can also include developmental data, such as an indication that the supervised person achieved a developmental milestone such as reading, using the restroom alone, expressed object permanence, and the like. The data uploaded by another controlling person and/or supervising person can also include social data, such as pictures of the supervised person during a day trip. For example, if the supervising persons take the supervised person on a day trip to a notable place, they can capture and upload images of the supervised person. The controlling person can then view and/or save the images using the fourth module 316.

In the fifth module 318, the controlling person can view recommendations generated by an artificial intelligence and/or machine learning ("AI/ML") model. The AI/ML recommendations can include suggested activities to maintain and/or guide development of the supervised person based on data from the wearable sensor. Purely by way of example, the AI/ML models may recognize that the supervised person is not getting enough exercise and recommend additional exercise time be incorporated into the child's day. In another example, the AI/ML models may recognize times when the supervised person is more likely to rest well and suggest those times for naps to maximize sleep and recovery for the supervised person during nap time. In yet another example, the AI/ML models may recognize a lack of emotional development in the supervised person and suggest additional social interaction with the supervised person (e.g., from additional talking around the supervised person, additional time spent with other supervised persons, and/or reading additional stories to the supervised person).

In the sixth module 320, the controlling person can connect other controlling persons (referred to as a "peer-to-peer network" of controlling persons) to request help and/or share supervision responsibilities over one or more supervised persons. For example, a parent, acting as a controlling person, can access the sixth module 320 while in a park to connect with other parents to facilitate supervision of groups of children while they play. In another example, the controlling person can access the sixth module 320 module for peer-to-peer help in an emergency, such as when the supervised person has unexplainably broken a geofence boundary and needs to be retrieved. The controlling person can also use the sixth module 320 to share reviews of public spaces, events, care providers, medical providers, and the like. The controlling person can also use the sixth module 320 to share articles related to supervised persons (e.g., articles on child development). The controlling person can also use the sixth module 320 to for various social purposes, such as to establish friend/trusted connections with other controlling persons in a social network framework (e.g., allowing parents on the system 100 (FIG. 1) to connect with other parents on the system 100 for any of the purposes discussed above).

Figure 4:
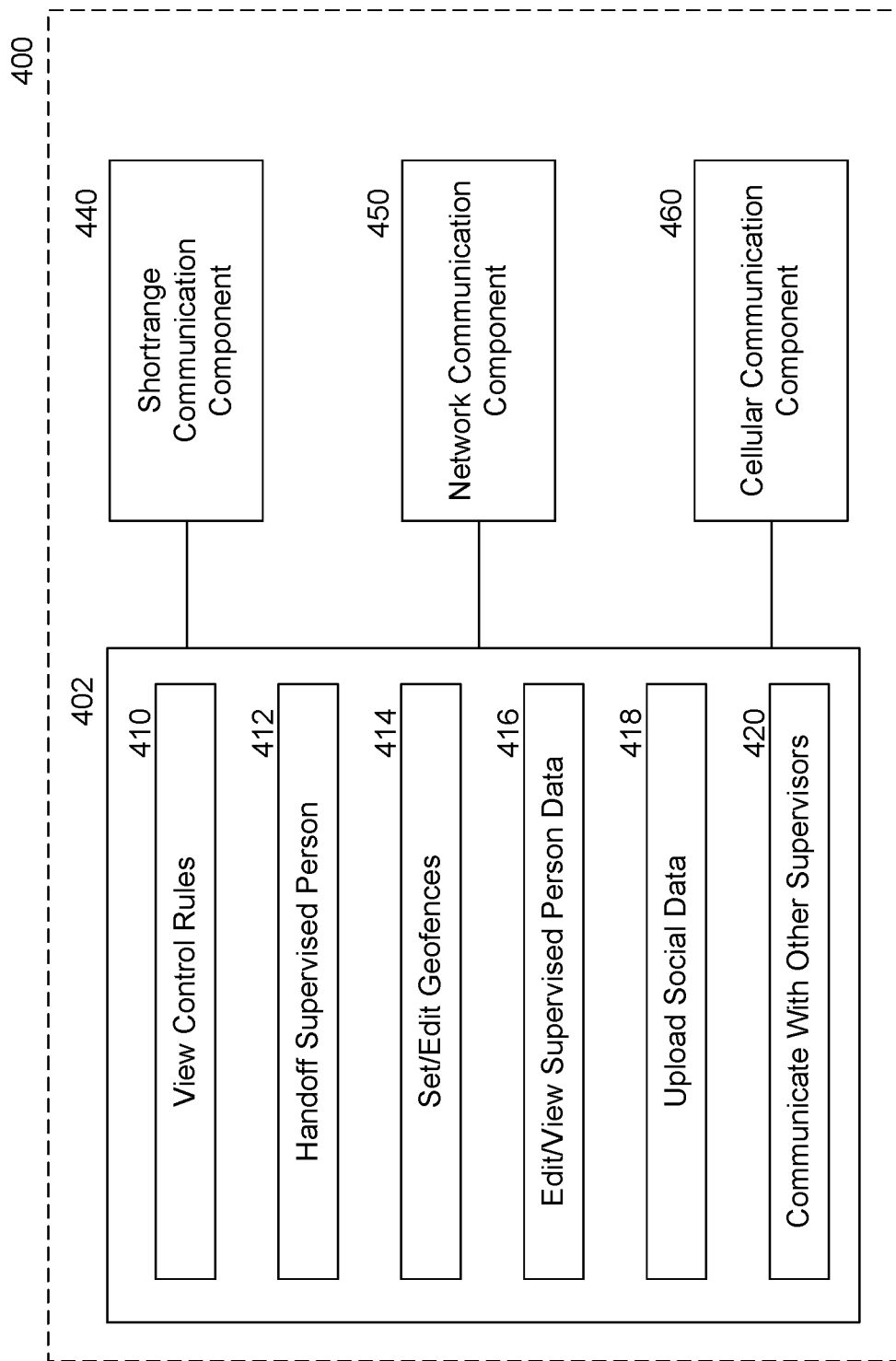
FIG. 4 is a schematic diagram of a platform for a supervising person in the system for monitoring a supervised person in accordance with some implementations of the present technology.

FIG. 4 is a schematic diagram of a subsystem 400 associated with a supervising person in a system for monitoring a supervised person in accordance with some implementations of the present technology. The subsystem 400 can be deployed in the electronic device 112 discussed above with respect to the system 100 of FIG. 1. Like the subsystem 300 discussed above with respect to FIG. 3, the subsystem 400 includes an operating platform 402 ("platform 402") with one or more modules (six shown, referred to individually as first-sixth modules 410-420), a shortrange communication component 440, an internet communication component 450, and a cellular communication component 460. Further, the platform 402 is operably coupled to each of the shortrange communication component 440, the internet communication component 450, and the cellular communication component 460, allowing the modules in the platform 402 to communicate with other subsystems and devices locally and/or over the network. Various examples of the modules are discussed in more detail below.

In the first module 410, supervising person can view the control rules set by a controlling person. For example, the supervising person can review rules related to where the supervised person can be taken without additional permission, whether the supervised person has a required nutritional diet, and/or whether the supervised person has a required nap time. In some implementations, the supervising person can set additional control rules through the first module 410. For example, the supervising person can add control rules for a subordinate supervising person, for example to further narrow the places the supervised person can be taken without additional permission.

In the second module 412, the supervising person can handoff the control over the supervised person from the supervising person to (and from) another supervising person and/or a controlling person. Various examples of the process for handing off control are discussed in more detail below with respect to FIG. 5.

In the third module 414, the supervising person can set, edit, and/or remove geofence boundaries. The geofence boundaries can be set, edited, and/or removed in a similar manner to any of those discussed above with respect to the third module 314 of FIG. 3. Similarly, in the fourth module 416, the supervising person can edit and/or view data related to the supervised person, such as any of the data discussed above with respect to the fourth module 316 of FIG. 3.

In the fifth module 418, the supervising person can upload social data related to the supervised person. Examples of social data can include pictures of the supervised person, a report on their daily activities (e.g., that a supervised person participated in a particular activity during play time), a report on observations of their favorite activities, who the supervised person interacts with, how the supervised person interacts with others, and/or various other data related to the social activities of the supervised person. The social data can be helpful for the controlling person(s) to understand the supervised person's interests and social development.

In the sixth module 420, the supervising person can communicate with other supervising persons. The communication can allow supervising persons to coordinate the control over one or more supervised persons. For example, the communication can allow supervising persons to account for needed breaks. The communication can also establish a secure channel to communicate regarding physical accidents, to report on broken geofence boundaries, and the like.

Figure 5:
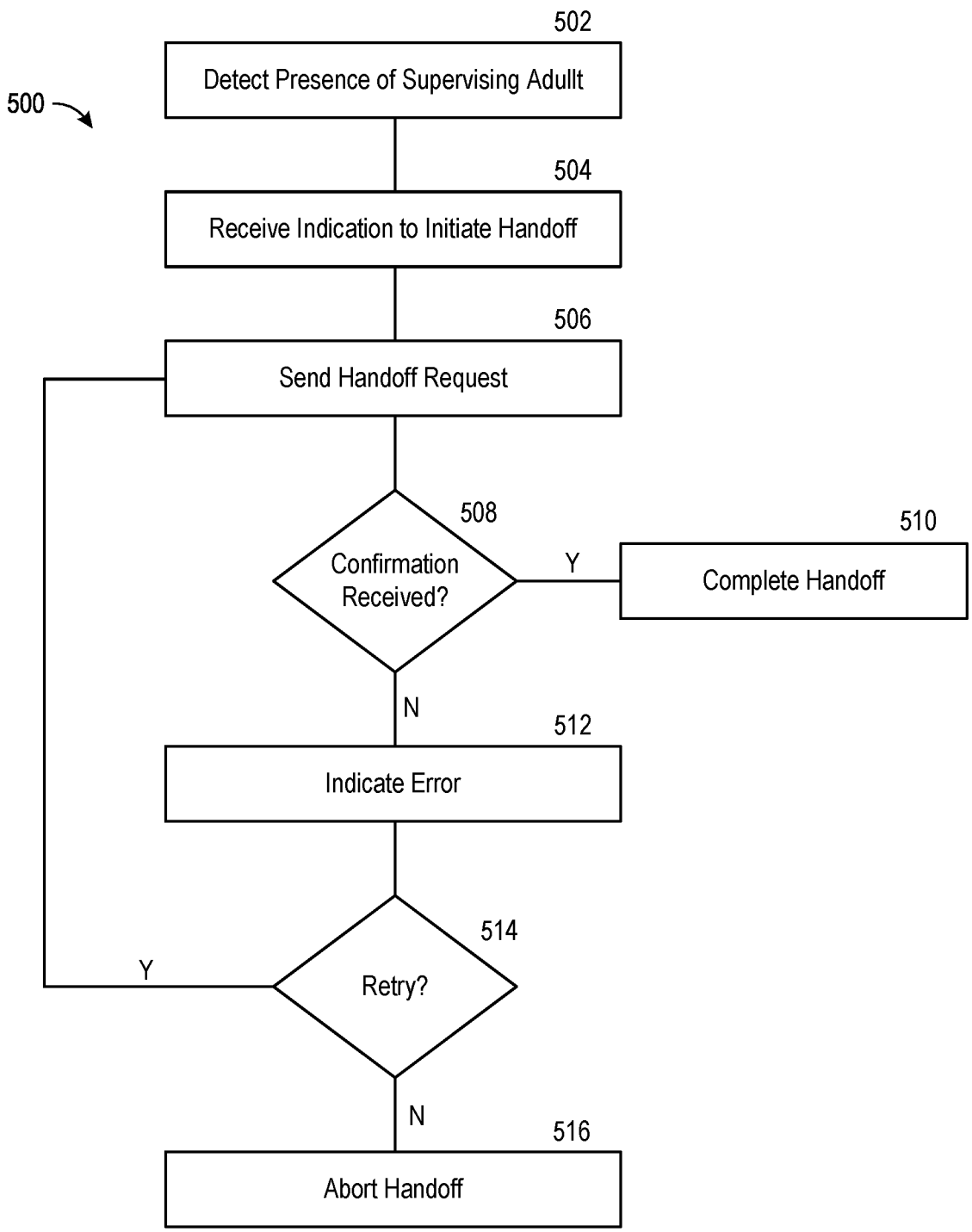
FIG. 5 is a flow diagram of a process for completing a handoff of the supervising responsibilities over a supervised person in accordance with some implementations of the present technology.

FIG. 5 is a flow diagram of a process 500 for completing a handoff of the supervising responsibilities over a supervised person in accordance with some implementations of the present technology. The process 500 can be executed by either of the subsystems 300, 400 described above to facilitate and record a handoff of the supervising responsibilities over of the supervised person. For example, the process 500 can be executed by the subsystem 300 to handoff the supervising responsibilities to a childcare provider. In another example, the process 500 can be executed by the subsystem 400 to handoff the supervising responsibilities from a first childcare provider to a second childcare provider (e.g., while the first childcare provider goes on break).

In the illustrated implementation, the process 500 begins at block 502 by detecting the presence of a receiving party (e.g., a supervising person and/or a controlling person). In various implementations, the presence of the receiving party can be detected using shortrange communication methods (e.g., via Bluetooth® communication), over a network connection (e.g., recognizing other electronic devices connected to the network), using location services enabled on two electronic devices, scanning a QR code associated with the receiving party (e.g., on the electronic device of the receiving party), and/or various other suitable methods. In some implementations, the presence of the receiving party is dependent on the receiving party's availability for a handoff. For example, if the supervising person is busy completing another handoff, their electronic device may appear as unavailable until the other handoff is completed, ensuring that the receiving party is cognitive of the present handoff as it is initiated and completed.

At block 504, the process 500 includes receiving an indication to initiate the handoff from the current supervisor to the receiving party. The handoff request includes an identification of the receiving party that allows the process 500 to identify and communicate with the receiving party (e.g., including an identification of an electronic device associated with the receiving party). In some implementations, the indication comes from an engagement with a user interface on an electronic device associated with the current supervisor, such as through an application on a current supervisor's smartphone. In various other implementations, the indication can be any other suitable gesture, such as a voice command received by the relevant electronic device, scanning a relevant code (e.g., a QR code) associated with the receiving party, aligning a portion of the receiving party's device with a portion of the current supervisor's device, and/or any other suitable gesture.

At block 506, the process 500 includes sending a handoff request to the receiving party. The handoff request can identify the supervised person, the current supervisor, a requested supervisory period, rules for the supervision, an ID for the current supervisor, a passcode for the handoff, a passcode for the supervised person, a passcode for the receiving party, a location for the handoff, and/or any other relevant information. In some implementations, the handoff request is a message sent to the receiving party (e.g., through a cellular messaging service, a push notification, and the like). In some implementations, the handoff request is sent to the receiving party through a user interface associated with the system (e.g., through an application on the electronic device). In some implementations, the handoff request includes a request for confirmation of reception of the supervised person. For example, the handoff request can instruct the receiving party to "read" (e.g., via shortrange communications) a unique identifier stored on a wearable device on the supervised person and communicate the unique identifier back to confirm the handoff. In another example, the confirmation can include an affirmative acknowledgement from the receiving party. In some implementations, the handoff request includes additional data related to the supervision being requested. For example, the handoff request can include an location for the next handoff, the date and time of the hand off, the expected amount of time for the requested supervision, the expected location for the supervision, an ID for the supervised person (e.g., when a current supervisor is responsible for multiple supervisors and/or the receiving party is associated with multiple supervised person, such as in a handoff between a parent with multiple children), a special message (e.g., a heads-up about the supervised person's current behavior, events in the supervised person's life that may affect their behavior, a change to a daily routine (e.g., when a parent will pick up their child early for an appointment), a full day report for the supervised person, and the like), and/or any other information relevant to the subject handoff and/or the expected supervision.

At decision block 508, the process 500 checks whether a confirmation of the handoff was received. In some implementations, the check is completed using a response received to the request to handoff. In some implementations, the check is completed after a predetermined amount of time to engage a timeout process for the request. In various implementations, the predetermined time can be based on a default value (e.g., 10 seconds, 30 seconds, 1 minute, 5 minutes, or any other suitable increment of time), a preferred value set by the current supervisor, a default value set by the receiving party, a default value set by an organization the receiving party works for (e.g., set by a daycare for all daycare workers), and/or set based on other suitable input. In some implementations, the predetermined time is at least partially dependent on the responsible parties involved, the date, the time of day, the location, the proximity of the responsible parties, and/or any other suitable factor. If a confirmation of the handoff was received, the process 500 continues to block 510 to complete the handoff process.

Completing the handoff can include updating a record of the supervising responsibilities to reflect the receiving party. In some implementations, as discussed above, the record is stored in the remote server 140 (FIG. 1). In some implementations, the record in stored on a secure ledger (e.g., a blockchain ledger), to increase the security of the record of the supervising responsibilities over the supervised person. In some such implementations, the ledger is accessible for review through the remote server 140 (FIG. 1). Completing the handoff can also include sending a notification of the completion to one or more parties in the system. For example, in a handoff between a controlling person and a supervising person, each of the parties can receive a confirmation of the handoff. Completing the handoff can also include sending a confirmation to one or more controlling persons, regardless of whether they were involved in the handoff. The confirmation can allow, for example, a parent to know who is responsible for the supervision of their child throughout the day in case they need to contact the supervising person and/or to provide some piece of mind to the parent.

Alternatively, if no confirmation as received at decision block 508, the process 500 continues to block 512 to indicate the error to the current supervisor and to prompt the current supervisor to maintain supervision over the supervised person. In various implementations, the indication of the error can be a push notification, message, or alert in the user interface. In some implementations, the indication of the error includes a reason for the error, such as a timeout of the request to handoff, a denial, a failure to send the request to handoff, a failed delivery of the request to handoff, a rule forbidding the handoff (e.g., when a particular receiving party is not allowed under the control rules for the supervised person), and the like.

At decision block 514, the process 500 checks whether the current supervisor wants to retry the handoff. The check can include prompting the current supervisor via a push notification, message, and/or prompt in the user interface and receiving a response. If the current supervisor indicates to retry the handoff, the process 500 can return to block 506 to send another handoff request to the receiving party. If the current supervisor indicates to not retry, the process 500 continues to block 516. If no response is received within a predetermined period, the process 500 can treat the lack of a response as an indication to not retry and continue to block 516.

At block 516, the process 500 aborts the handoff. In some implementations, the attempted handoff and failure is added to the record of the supervising responsibilities. Recording the attempted handoff and/or failure can help maintain a complete record of the chain of custody and/or help identify gaps in the chain of custody. For example, the record of attempts and/or failures can help identify points where the process 500 may have failed but the supervised person was handed off in the real world. In addition, the record of attempts and/or failures can allow a controlling person to identify attempted, non-allowed handoffs (e.g., where a handoff fails because the receiving party is not authorized). These attempts may reflect a point of discussion with the supervising party responsible when the attempt was made, for example to explain why a particular receiving party is not authorized to supervise the supervised person.

Figure 6:
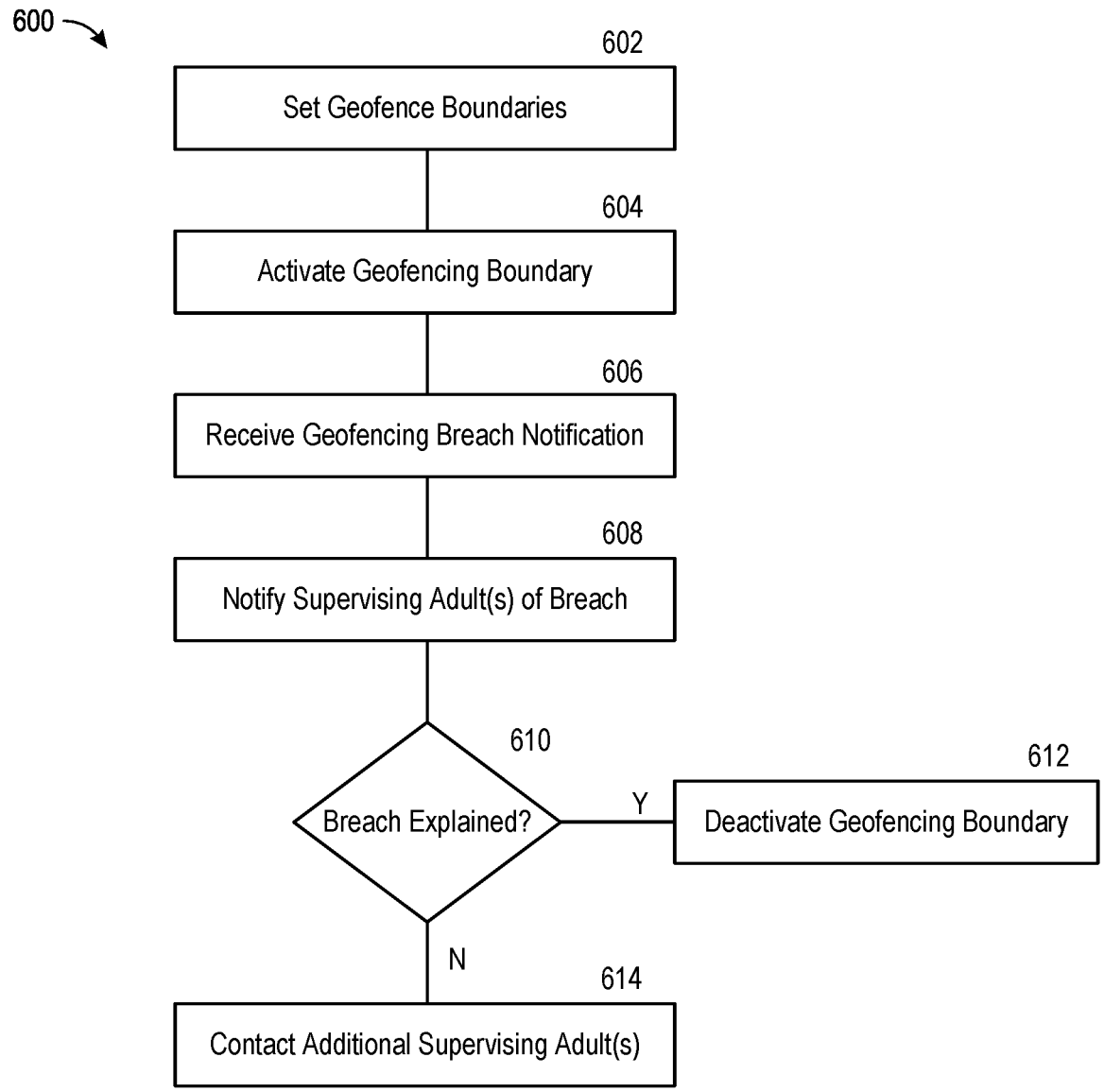
FIG. 6 is a flow diagram of a process for monitoring a geofencing boundary in accordance with some implementations of the present technology.

FIG. 6 is a flow diagram of a process 600 for monitoring a supervised person within a geofencing boundary in accordance with some implementations of the present technology. The process 600 can be executed by either of the subsystems 300, 400 (FIGS. 3 and 4) and/or by a component of the remote server 140 (FIG. 1) to ensure the supervised person stays within a predetermined boundary during a set period. For example, the process 600 can be executed by the subsystem 300 to set a boundary line around a public park during a visit to the park; by the subsystem 400 to set a boundary line around a playground during a recess period;

by the remote server 140 during a recurring period (e.g. weekly daycare); and the like.

The process 600 begins at block 602 to set a geofence boundary. The geofence boundary can be set through a user interface by drawing a boundary line on a map, selecting one or more preset boundaries (e.g., selecting a public park in a map that includes preset boundaries for the public park, selecting one or more saved geofences, and the like), indicating a radius around a selected location, indicating a radius around a selected supervising party, placing one or more IoT devices and/or beacons to define a perimeter, and/or any other suitable mechanism. In some implementations, setting the geofence boundary can require that the relevant party have authorization to set the boundary. For example, a controlling person 110 (FIG. 1) may limit the permissions for which supervising persons 120 can set a geofence boundary to require specific supervisors (e.g., a head supervisor) to do so. In some implementations, anew geofence boundary is limited to being within a previously set geofence boundary. For example, a controlling person 110 (FIG. 1) may set a first geofence boundary when dropping their toddler off at a childcare facility, thereby limiting any supervising persons 120 to setting a second geofence boundary within the first geofence boundary (e.g., around a playground or specific room in the childcare facility).

At block 604, the process 600 includes activating the geofencing boundary. Once activated, components of the supervising system (e.g., the system 100 illustrated in FIG. 1) can require that a wearable device on the supervised person report on the position of the wearable device. The reports can periodic (e.g., once per minute, twice per minute, once every five minutes, and/or any other suitable interval) or continuous. The report can include an indication of a connection to an electronic device and/or network, allowing the system to roughly determine the position of wearable device. The report can also include an exact location of the wearable device with respect to a network, various electronic devices, and/or on earth (e.g., using GPS coordinates). The reports allow the supervising system to monitor whether the wearable device has breached the geofencing boundary.

If the wearable device remains within the geofencing boundary, no further actions occur in the process 600. In some implementations, the geofencing boundary is then later deactivated based on an indication from a supervising party with the appropriate authorizations. In some implementations, the geofencing boundary is set with a predetermined time window (e.g., during a recess period, during daycare hours, for an hour while at a park, and the like). At the end of the predetermined time window, the geofencing boundary can then be deactivated.

At block 606, the process 600 includes receiving a geofencing breach notification. The geofencing breach notification can include a time stamp for the breach, an indication of where the breach occurred, an indication of the current location of the wearable device, an indication of the adults currently responsible for the supervised person, and/or an indication of nearby adults. The geofencing breach notification can also include data from the wearable sensor, such as data on the supervised person's heart rate, temperature, emotional state, and the like.

At block 608, the process 600 includes notifying the controlling and/or supervising person(s) of the breach. For example, as discussed above, the process 600 can be executed either of the subsystems 300, 400 (FIGS. 3 and 4) and/or by a component of the remote server 140 (FIG. 1). Accordingly, in implementations in which the geofencing breach notification is received by the cloud server and/or the electronic device of a party not currently responsible for the supervised person, the process 600 can send a notification to the currently responsible party at block 608. For example, the controlling person may set the geofencing boundary through their electronic device, which can then receive the geofencing breach notification and notify a supervising person that is currently responsible for the supervised person. In implementations in which the geofencing breach notification is received by the electronic device of the party that is currently responsible, the notification can include any suitable alert (e.g., push notification, alarm sound, voice call, and the like) to direct the attention of the party that is currently responsible.

At decision block 610, the process 600 checks whether the breach of the geofence boundary is explained. If the breach is explained, the process 600 continues to block 612 to deactivate the geofencing boundary; else the process continues to block 614 to notify one or more additional adults. In some implementations, the check includes prompting the currently responsible party for an input on whether the breach is explained. In some implementations, the input includes a yes/no response. In some implementations, the input includes a brief explanation that can be recorded in the system 100 (FIG. 1) and/or sent to interested parties. Purely by way of example, the breach can be cause by a supervised person visiting a restroom outside of a defined geofence while a supervising person is responsible. The explanation can reflect the restroom visit, allowing a controlling person to review the explanation and quickly understand the reason for the geofencing breach. In another example, the explanation can reflect an early departure from a geofenced area when the responsible party forgets to deactivate the geofencing boundary (e.g., when a visit to a park ends early).

As discussed above, if the geofencing boundary is explained, the process continues to block 612. At block 612, the process 600 includes deactivating the geofencing boundary to reflect the explained breach. The deactivation can be recorded in the remote server 140 (FIG. 1), allowing interested parties to review the updated status of the geofencing boundary. In some implementations, the deactivation is temporary. For example, where the breach is explained by a temporary need (e.g., to use a restroom outside the geofencing boundary), the deactivation at block 612 can last a predetermined time reflecting the need. At the end of the predetermined time, the process 600 can return to block 604 to re-activate the geofencing boundary. A continued breach will then result in a geofencing breach notification requiring further explanation. In some implementations, once the geofencing boundary is deactivated at block 612, the process 600 must start again at block 602 to reactivate a geofencing boundary.

Alternatively, if the geofencing boundary is not explained, the process continues to block 614. At block 614, the process 600 includes contacting one or more additional adults. The additional adult(s) can include the controlling persons (e.g., to notify parents of the unexplained breach); other controlling and/or supervising person(s) associated with the currently responsible party (e.g., to notify other childcare providers in a childcare center); other, unrelated adults (e.g., alerting other parents that also use the system 100 (FIG. 1)); and/or emergency responders (e.g., security officers, the police, fire departments, neighborhood watch, and the like) to broaden the network of adults that can respond to the breach. In some implementations, the number and/or type of adults contacted is dependent on inputs from the responsible party and/or a controlling person. For example, when the breach notification indicates that the supervised person is outside a geofenced area but still within a childcare facility, the responsible party can elect to contact other supervising persons (e.g., other childcare providers) but not the controlling persons (e.g., parents) or emergency responders to avoid unnecessary alerts.

In some implementations, the process 600 then returns to decision block 610 to check whether the breach is explained. Continuing the example above, after additional childcare workers are contacted, they may be able to retrieve the supervised person and provide an explanation for the breach. The explanation can then be recorded and/or later reviewed by any interested party (e.g., by a parent reviewing the breach). If the breach is still unexplained, the process 600 can return to block 614 to contact one or more additional adults. In some implementations, the process 600 can continue on a loop between decision block 610 and block 614 and escalate the number and/or type of adult(s) contacted each pass through the loop. Continuing the example above, if none of the childcare workers can explain the breach, the process 600 can contact the controlling person (e.g., a parent); and if the controlling person cannot explain the breach, the process 600 can contact one or more emergency responders (e.g., security officers, the police, community response team, neighborhood watch, and the like). In such implementations, the loop ends either when the breach is explained or the final, most serious group of additional adults (e.g., emergency responders) is contacted.

Figure 7A:
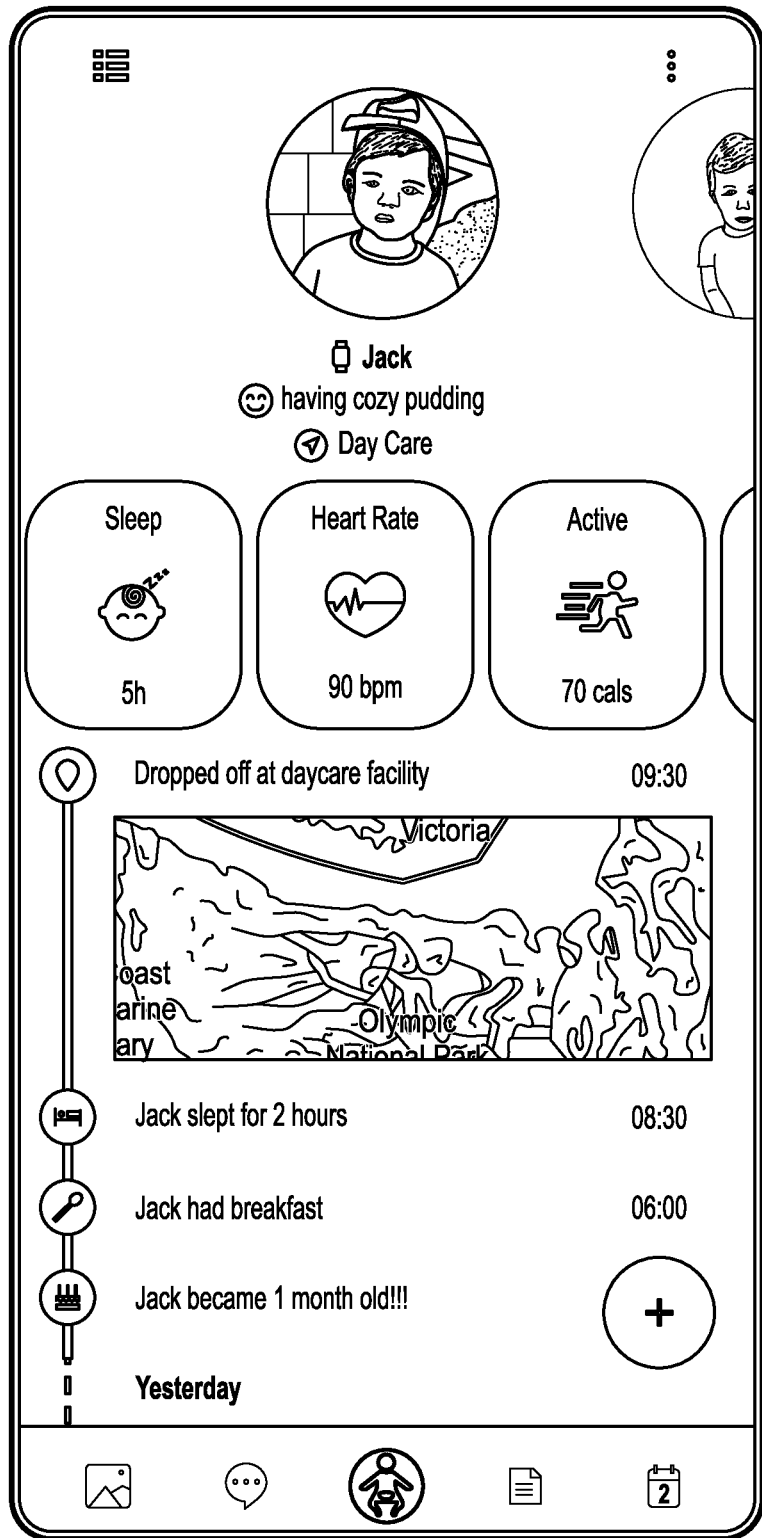
FIGS. 7A-7H are wireframes of various user interfaces associated with the system for monitoring a supervised person in accordance with some implementations of the present technology.

FIGS. 7A-7H are examples of various user interfaces associated with the system for monitoring a supervised person in accordance with some implementations of the present technology. For example, FIG. 7A illustrates an example user interface 700a communicating various information related to the current supervision and status of a toddler. In the illustrated implementation, the user interface 700a includes an indication of the toddler's current mood (e.g., having cozy pudding) and current location (e.g., at daycare). The user interface 700a also includes an indication of various bioindicators from a wearable device on the toddler (e.g., a measure of the amount of sleep the toddler got, when they had their last nap, their current heart rate, and how active they have been). The user interface 700a also includes a record of various relevant events, such as the age of the last handoff of control over the toddler, meals, their age, and the like.

Figure 7B:

FIG. 7B illustrates an example user interface 700b for viewing photos of the supervised person. The photos can be organized into albums by date, category, photographer, location, and/or any other suitable category. Further, as discussed above, the photos can be added by any responsible party with access to the photo albums. For example, the user interface 700b allows parents to review photos of their children that are captured by a daycare worker during a field trip with the children.

Figure 7C:
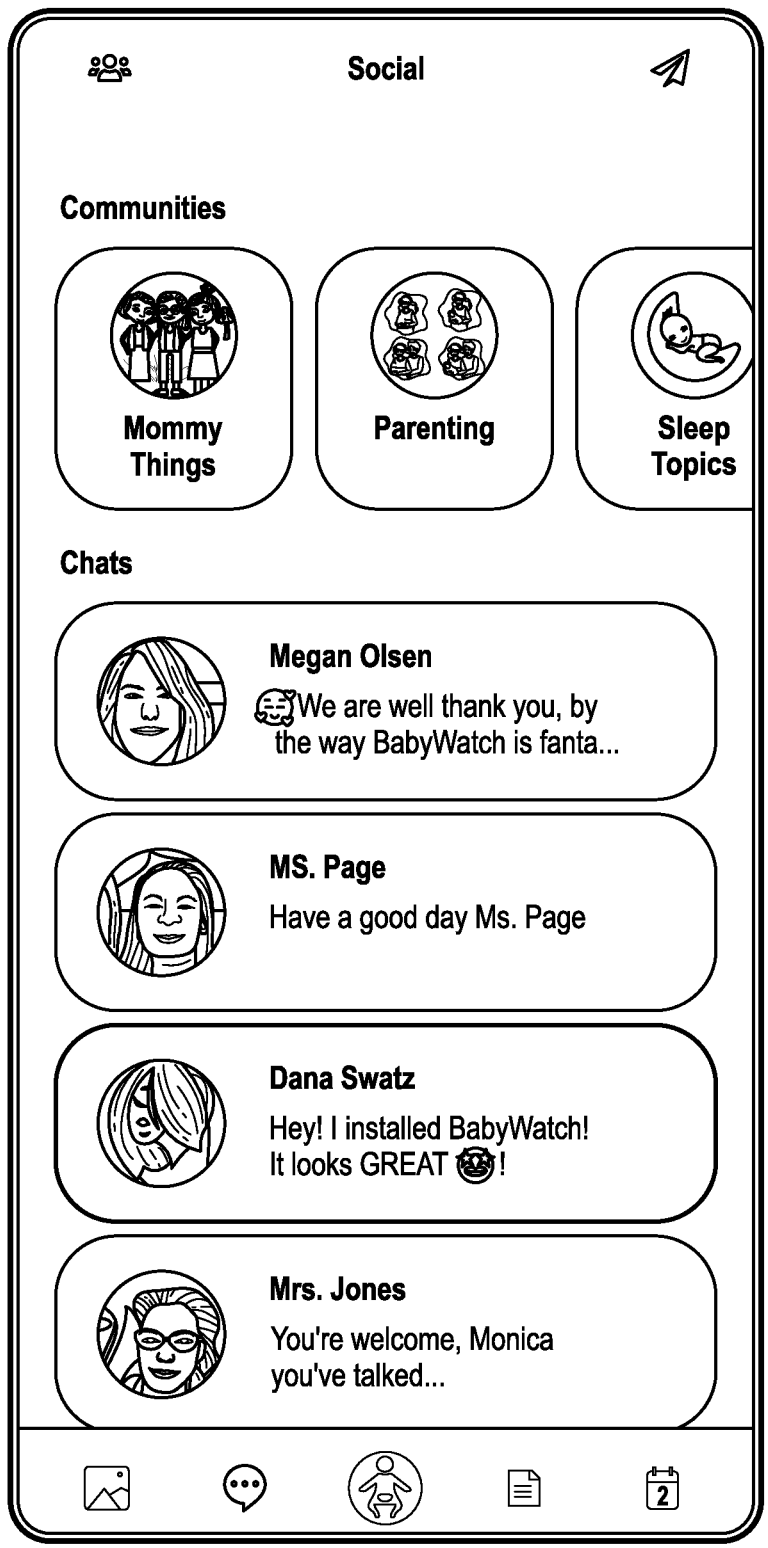

FIG. 7C illustrates an example user interface 700c associated with a peer-to-peer network. In the illustrated implementation, the user interface 700c enables a controlling person to enter into and participate in various communities. The communities can be organized around specific topics, activities, interests, and/or any other suitable category. The user interface 700c also enables the supervised person to connect directly with one or more additional controlling persons and/or one or more supervising persons. Purely by way of example, the user interface 700c allows a parent to connect with another parent to share developmental tips, reviews of activities, locations, and/or childcare providers, and/or to request help (e.g., when a child wanders away). The user interface 700c can also allow a parent to connect with other parents to establish a social network of other parents connected to the system 100 (FIG. 1).

Figure 7D:
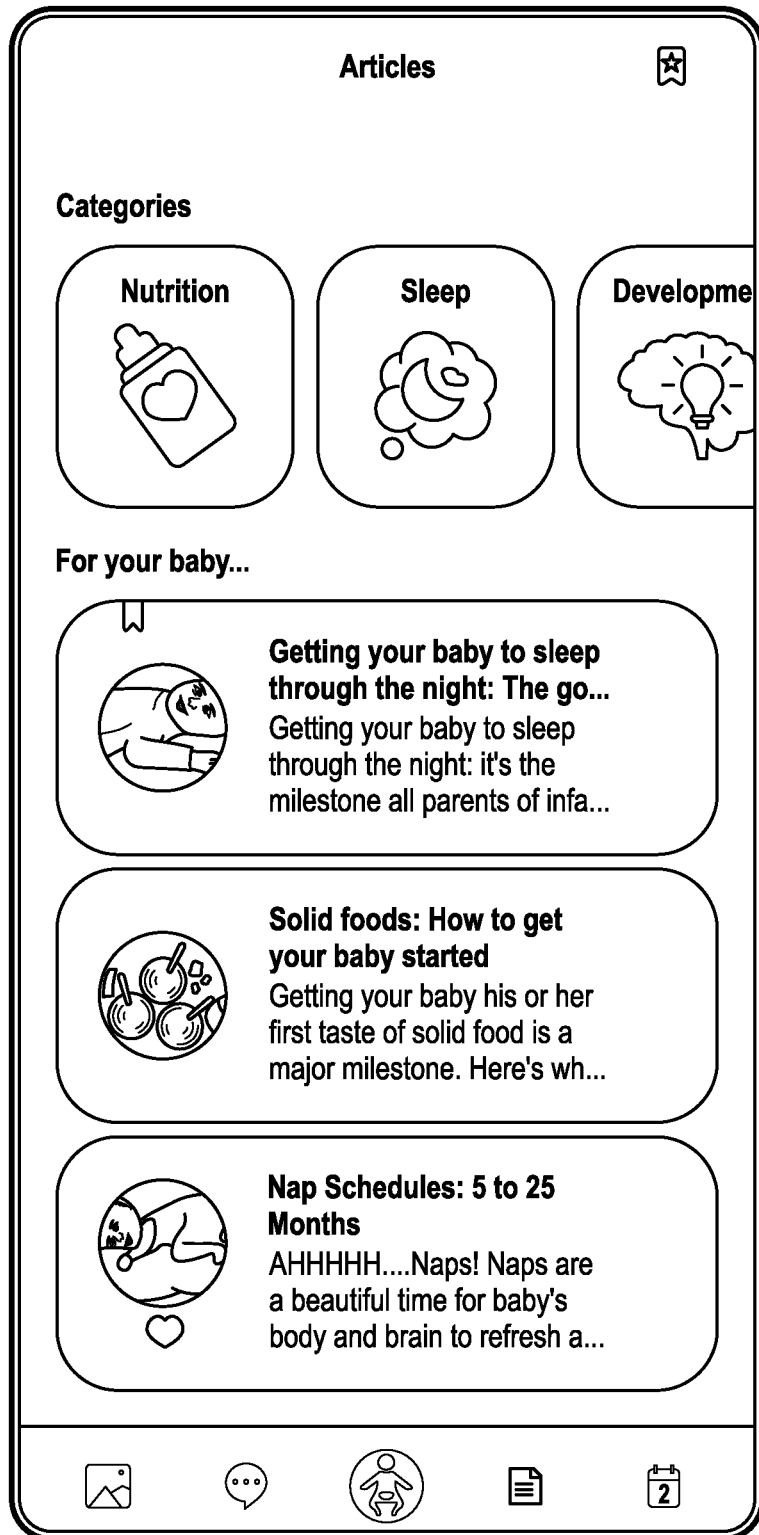
Figure 7E:
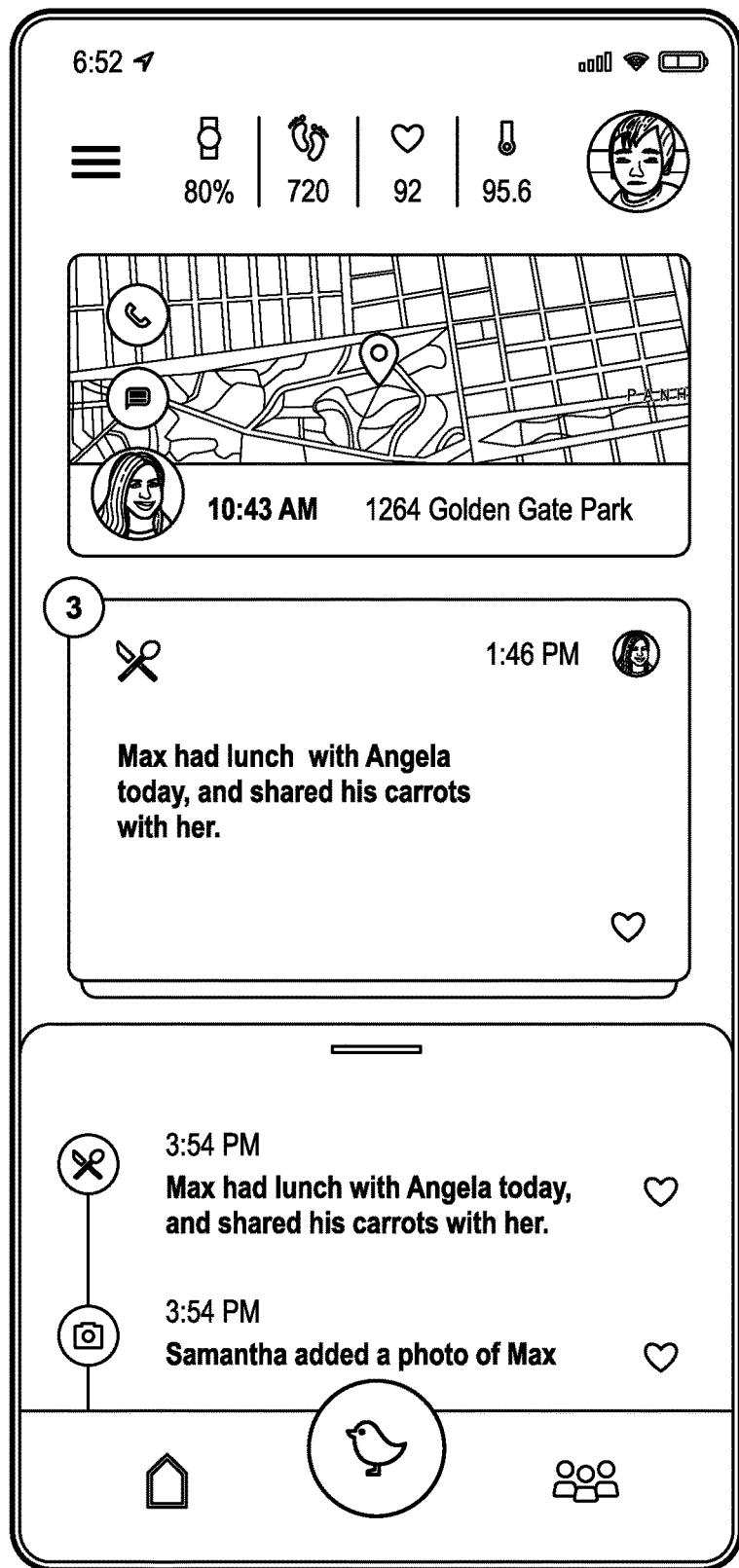
Figure 7F:
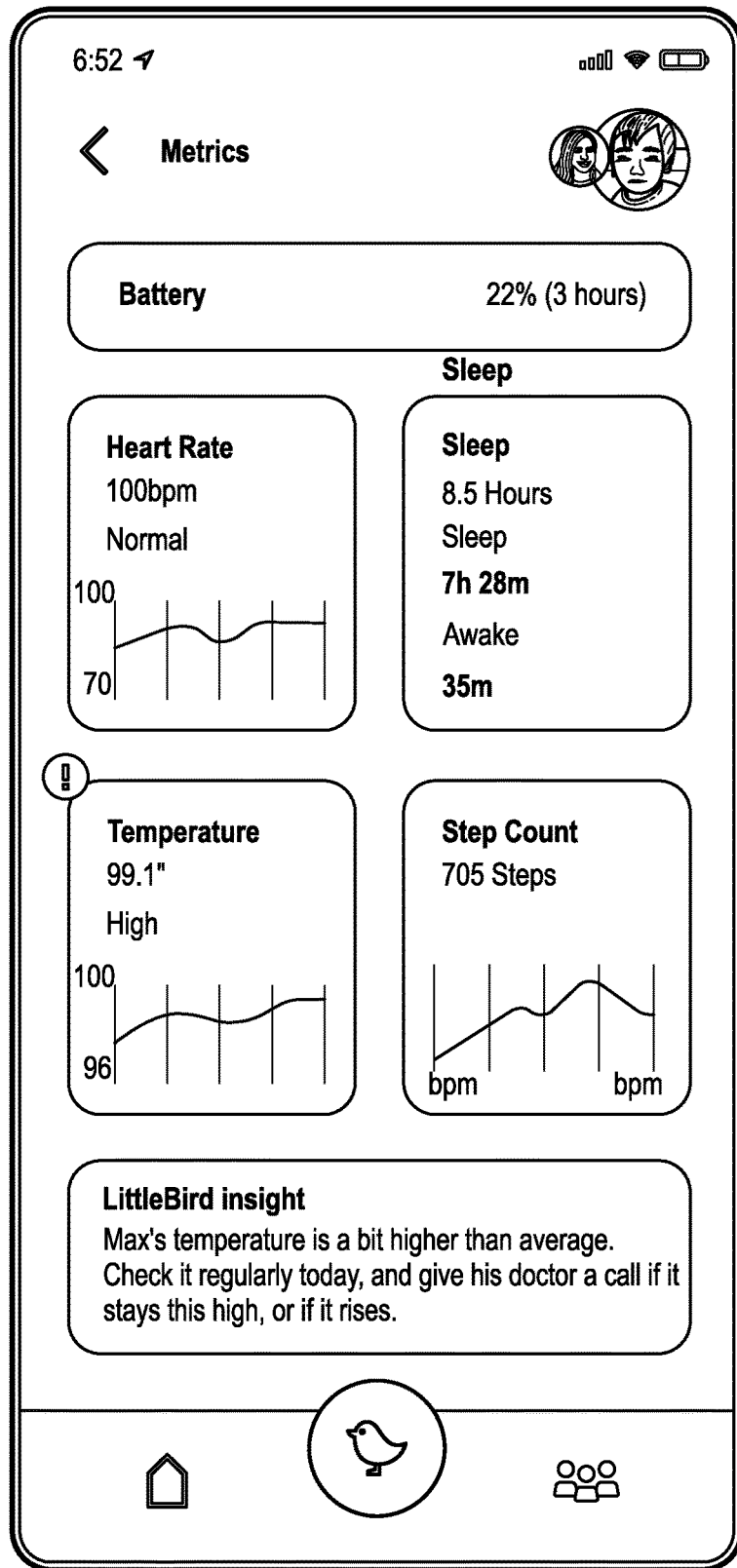
Figure 7G:
Figure 7H:
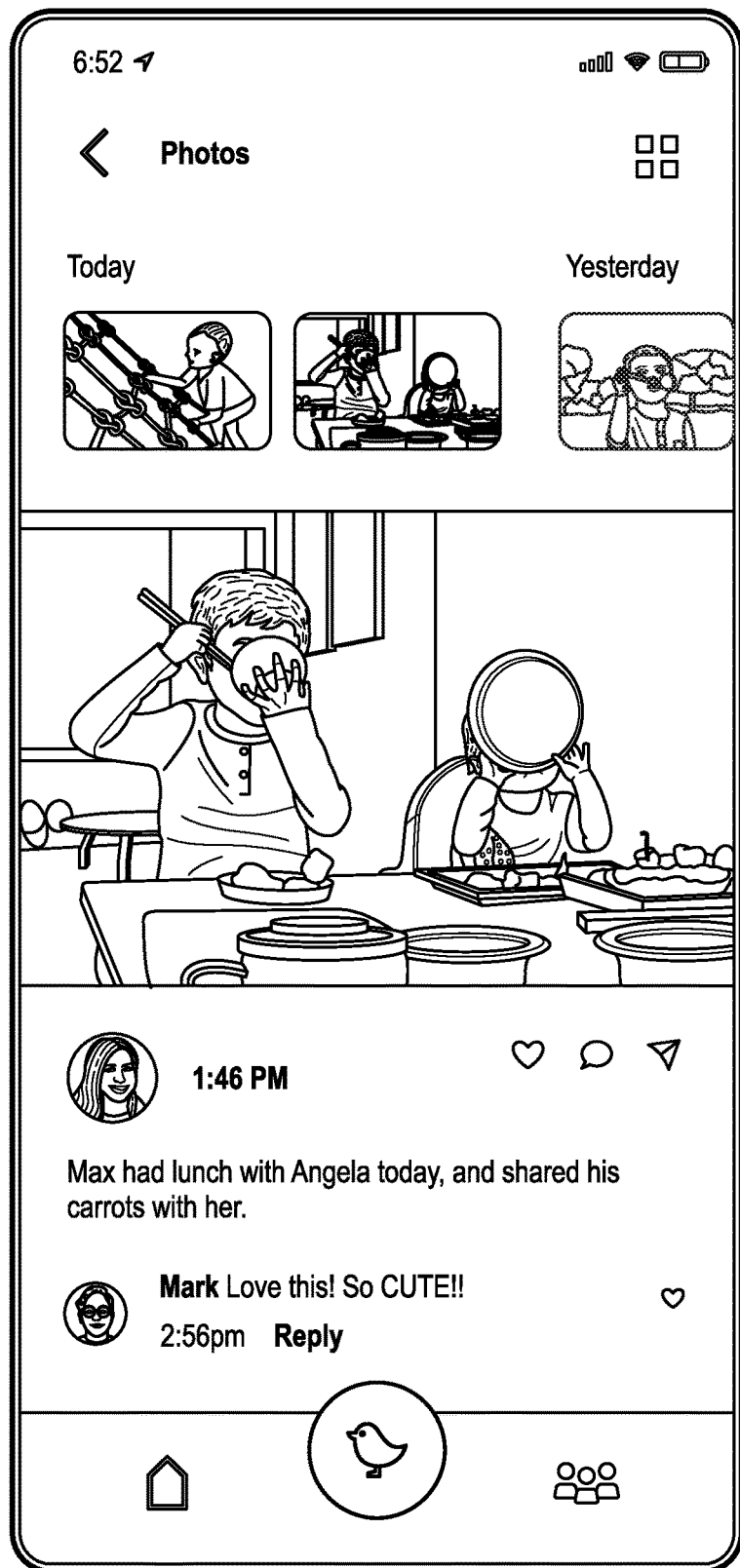

FIG. 7D illustrates an example user interface 700d associated with AI/ML recommendations for controlling persons. In the illustrated implementation, the user interface 700d includes categories of topics that are identified as relevant for a specific controlling parent along with various specific recommendations that are specific to the supervised person. As discussed above, the recommendations can be identified based on data a responsible person uploads to the system regarding the supervised person and/or data collected by a wearable device on the supervised person. The recommendations can be related to the physical, emotional, and/or mental development of the supervised person, as well as recommendations for dynamically adjusting supervision of the supervised person over time.

FIGS. 7E-7H illustrate additional examples of user interfaces 700e-700h associated with the system for monitoring a supervised person. For example, each of the user interfaces 700e, 700f communicates additional data related to the supervised person such as their daily activities and/or bioindicators; the user interface 700g provides a direct connection between a controlling person (e.g., a parent) and supervising persons (e.g. childcare providers) to communicate regarding the status of the supervised person; and the user interface 700h can be accessed to view and/or photos of the supervised person.

Example Systems and Methods Related to the Wearable Device

Figure 8:
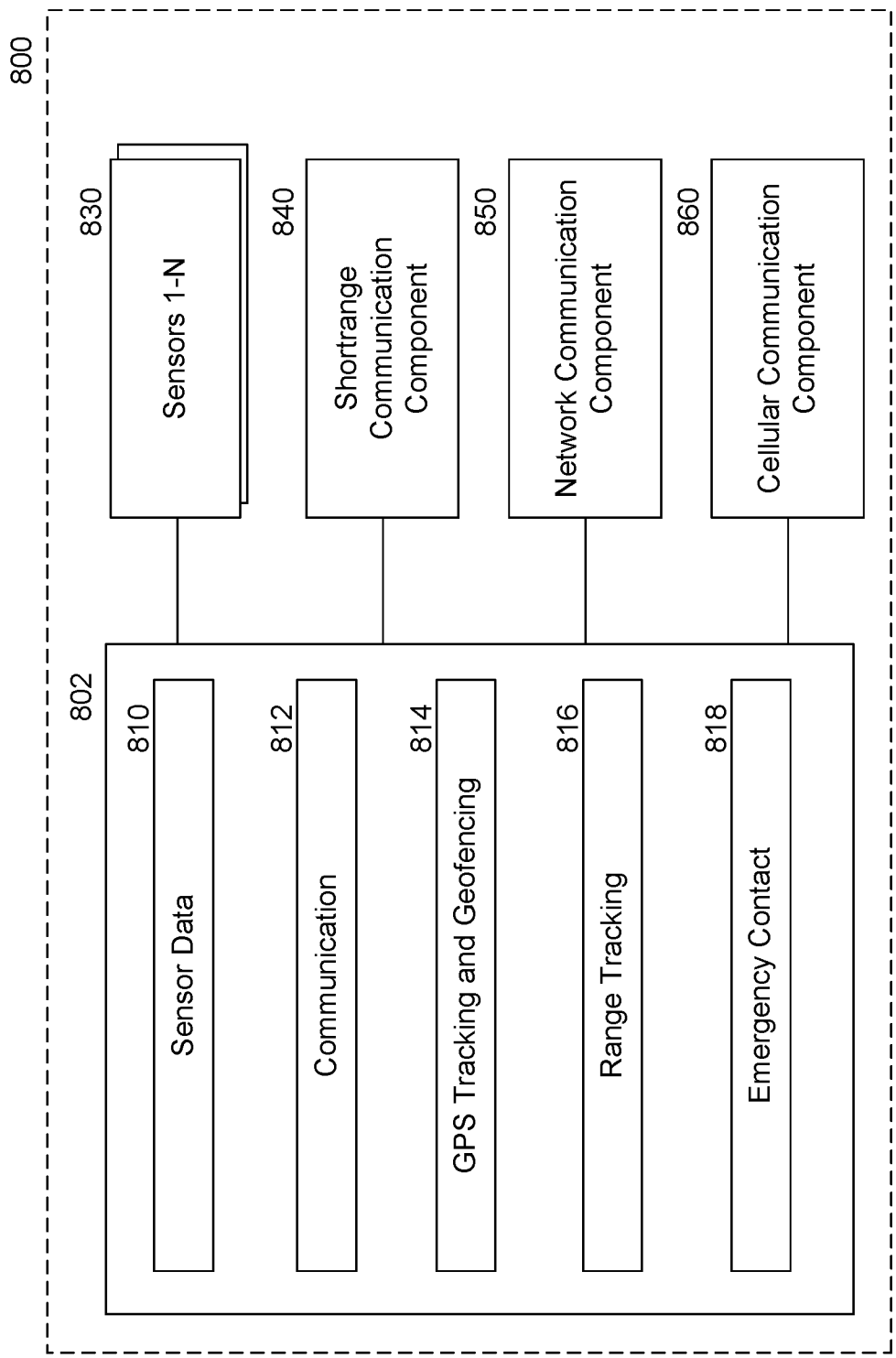
FIG. 8 is a schematic diagram of a platform for a wearable device for use by a supervised person in accordance with some implementations of the present technology.

FIG. 8 is a schematic diagram of a subsystem 800 associated with a wearable device for use on a supervised person in accordance with some implementations of the present technology. The subsystem 800 can be deployed in the wearable device 132 discussed above with respect to the system 100 of FIG. 1. Like the subsystems 300, 400 discussed above with respect to FIGS. 3 and 4, the subsystem 800 can include an operating platform 802 ("platform 802") with one or more modules (six shown, referred to individually as first-sixth modules 810-820), a shortrange communication component 840, an internet communication component 850, and a cellular communication component 860. Further, the subsystem 800 can include one or more sensors 830 (1-N indicated) that collect bioindicators while worn by the supervised person. Purely by way of example, the sensors 830 can include a PPG sensor, an accelerometer, a skin temperature sensor, a skin conductivity sensor, additional hydration sensors, heart-rate variability sensors, resting heart rate sensors, sweat chemical composition sensors, nervous system electrical sensors, air quality sensors, UV exposure sensors, sensors to detect environmental chemicals, blood oxygen and/or pulse oxygen sensors, voice recognition, electrocardiogram (ECG) sensor, pressure sensors, gyroscopes, magnetometers, and/or any combination therein. The PPG sensor allows the subsystem 800 to measure and record the supervised person's heart rate; the accelerometer allows the subsystem 800 to measure and record the supervised person's movement; the skin temperature sensor allows the subsystem 800 to measure and record the supervised person's temperature over time; and the skin conductivity sensor allows the subsystem 800 to measure and record the supervised person's level of psychological or physiological arousal, which is effected by the supervised person's cognitive activity and/or emotions.

As further illustrated in FIG. 8, the platform 802 is operably coupled to each of the one or more sensors 830, the shortrange communication component 840, the internet communication component 850, and the cellular communication component 860, allowing the modules in the platform 802 to communicate with other subsystems and devices locally and/or over a network.

The first module 810 allows the platform 802 to receive, organize, store, and/or communicate the data from the sensors. The data can include numerous different bioindicators, such as any of the bioindicators from the sensors discussed above. In some implementations, the first module 810 also at least partially processes and/or links the data. For example, the first module 810 can receive data from a skin conductivity sensor, process the data to determine related cognitive activity and/or emotions, then communicate and/or store the determined cognitive activity and/or emotions. In another example, the first module 810 can link data from each of the sensors, for example allowing the data to be later reviewed and/or processed together.

The second module 812 allows the platform 802 to control the shortrange communication component 840 to search for a nearby subsystem and/or device (e.g., either of the subsystems 300, 400 discussed above) and/or communicate data from the sensors to the nearby subsystem and/or device.

The third module 814 allows the platform 802 to control the internet communication component 850 to communicate data from the sensors over a network (e.g., the network 290 discussed above). In some implementations, the platform 802 toggles the internet communication component 850 between an on and off position to conserve a battery life of the wearable device. For example, while a nearby subsystem and/or device is detected, the platform 802 can rely on a lower power consumption of the shortrange communication component 840 to communicate the sensor data and thereby take advantage of the power of the nearby subsystem and/or device to further communicate the sensor data. If no subsystem and/or device is detected nearby, the platform 802 can activate the internet communication component 850 to search for and connect to an available internet connection.

The fourth module 816 allows the platform 802 to control the cellular communication component 860 to communicate data from the sensors over a cellular network (e.g., thereby connecting to a broader network). In some implementations, the platform 802 toggles the cellular communication component 860 between an on and off position to conserve a battery life of the wearable device. For example, while a nearby subsystem and/or device is detected, the platform 802 can rely on a lower power consumption of the shortrange communication component 840 and/or the internet communication component 850 to communicate the sensor data. If no subsystem and/or device is detected nearby and no internet connection is detected, the platform 802 can activate the cellular communication component 860 to search for and connect to an available cellular network.

The fifth module 818 allows the platform 802 to communicate with a GPS satellite to track the location of the subsystem 800 and/or implement one or more geofence boundaries. In some implementations, the platform 802 controls an onboard GPS component to toggle the sensor between on and off positions. For example, while the platform 802 detects a nearby subsystem, device, and/or internet connection, the platform 802 can maintain the GPS component in an off position to conserve the battery life of the wearable device. When no such connections are detected, the platform 802 can toggle the GPS component to an on position. In some implementations, the platform 802 toggles the GPS component to an on position whenever a geofence boundary is activated by another component in the system 100 (FIG. 1). The activation of the geofence boundary can be communicated to the platform 802, for example, through any of the shortrange communication component 840, the internet communication component 850, and/or the cellular communication component 860.

The sixth module 820 allows the supervised person to activate an emergency contact function on the wearable device. In some implementations, the sixth module 820 automatically contacts a preselected party when activated (e.g., a controlling person, an emergency responder, and the like) to quickly connect the supervised person with the preselected party. In other implementations, the sixth module 820 allows the supervised person to select who to contact. In some implementations, the sixth module 820 cannot be activated absent certain bioindicators through the sensors 830. For example, unless data from the sensors 830 indicates an elevated heart rate, a high skin temperature, absence from a geofenced area, and/or abnormal mental and/or emotional conditions, the platform 802 can prevent the sixth module 820 from being activated. The requirement of certain bioindicators can help ensure that the supervised person does not superfluously activate the sixth module 820.

Figure 9A:
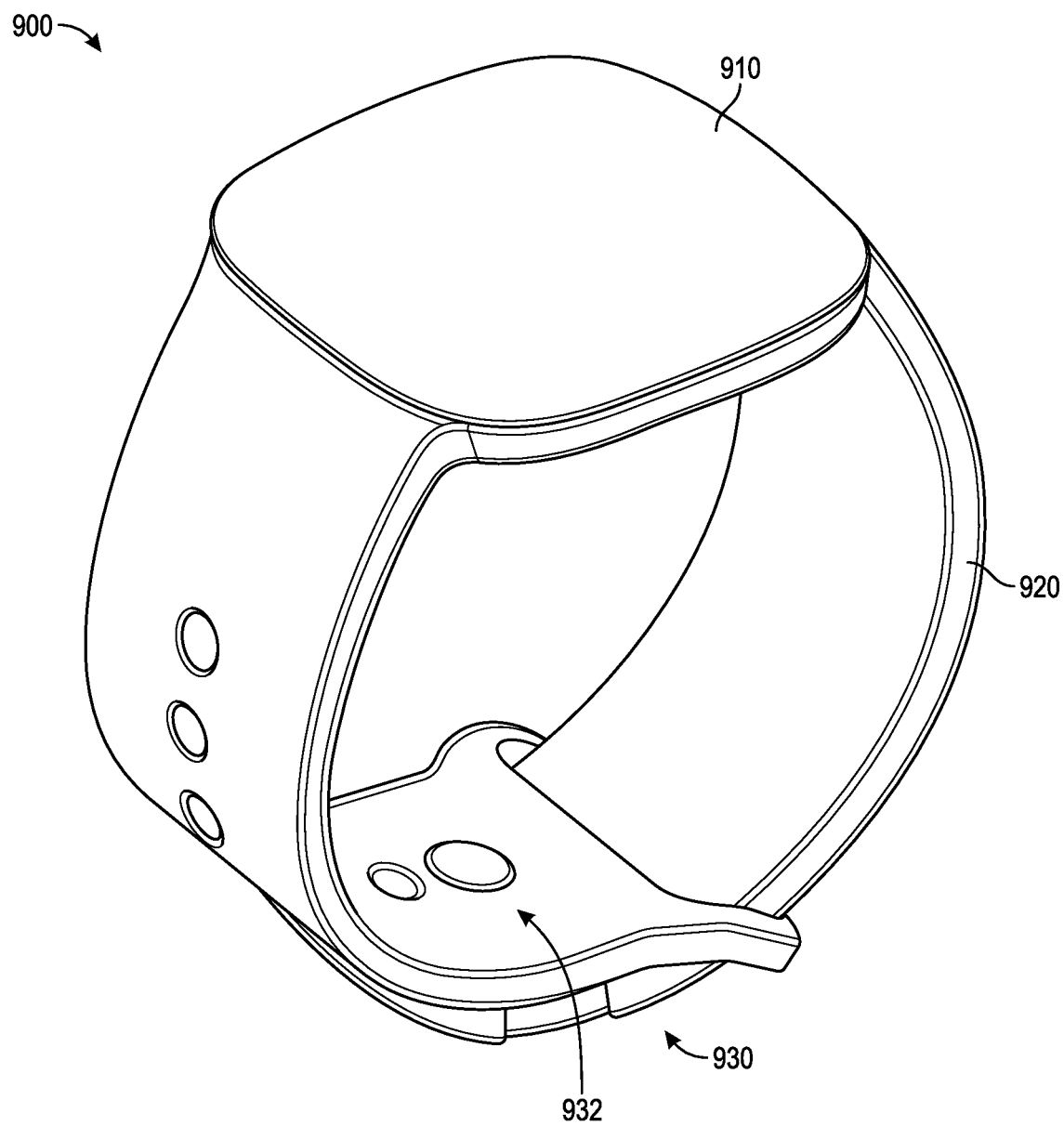
FIGS. 9A-9C are an isometric view, a bottom view, and a side view, respectively of a wearable device for use by a supervised person in accordance with some implementations of the present technology.
Figure 9B:
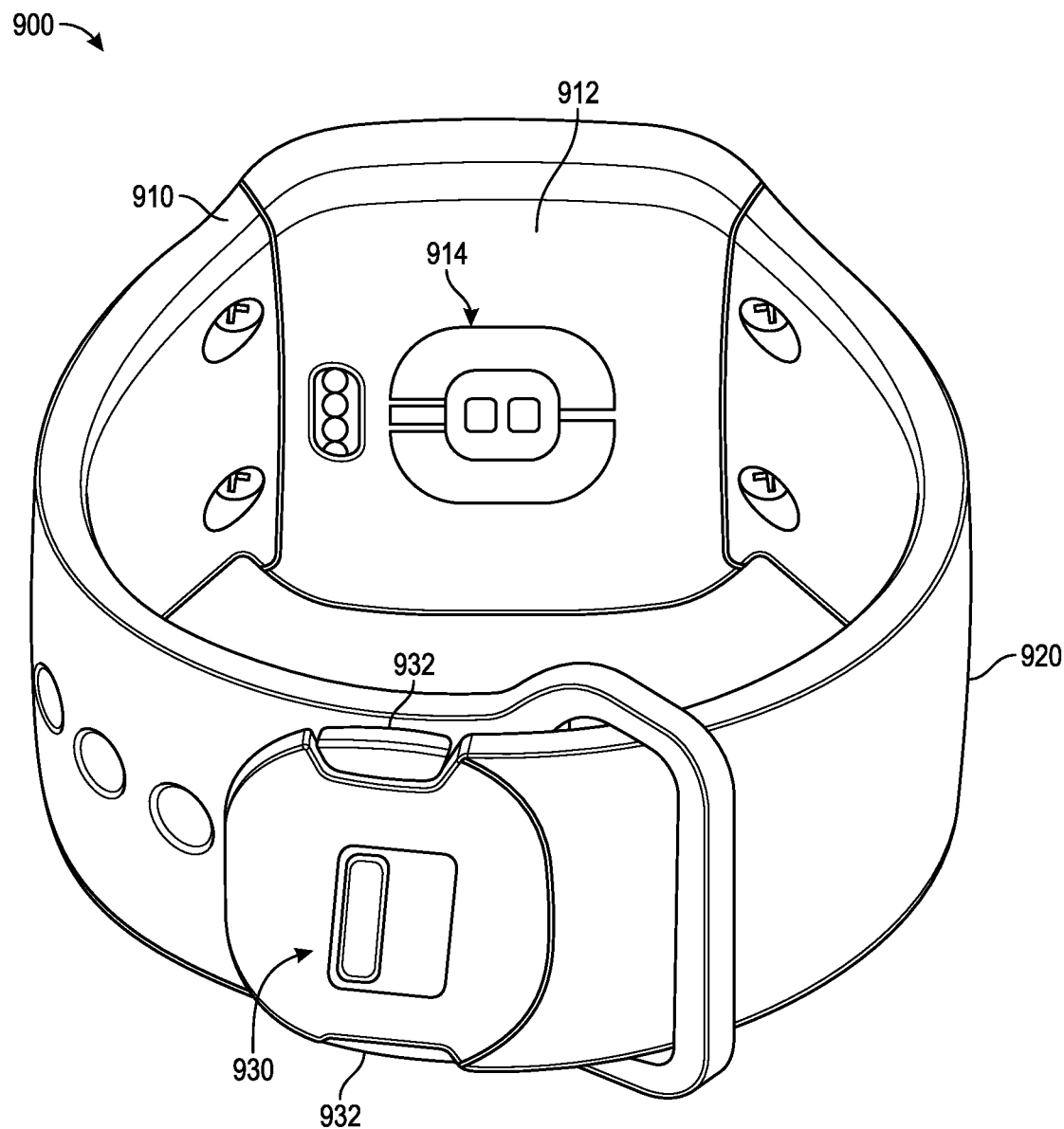
Figure 9C:
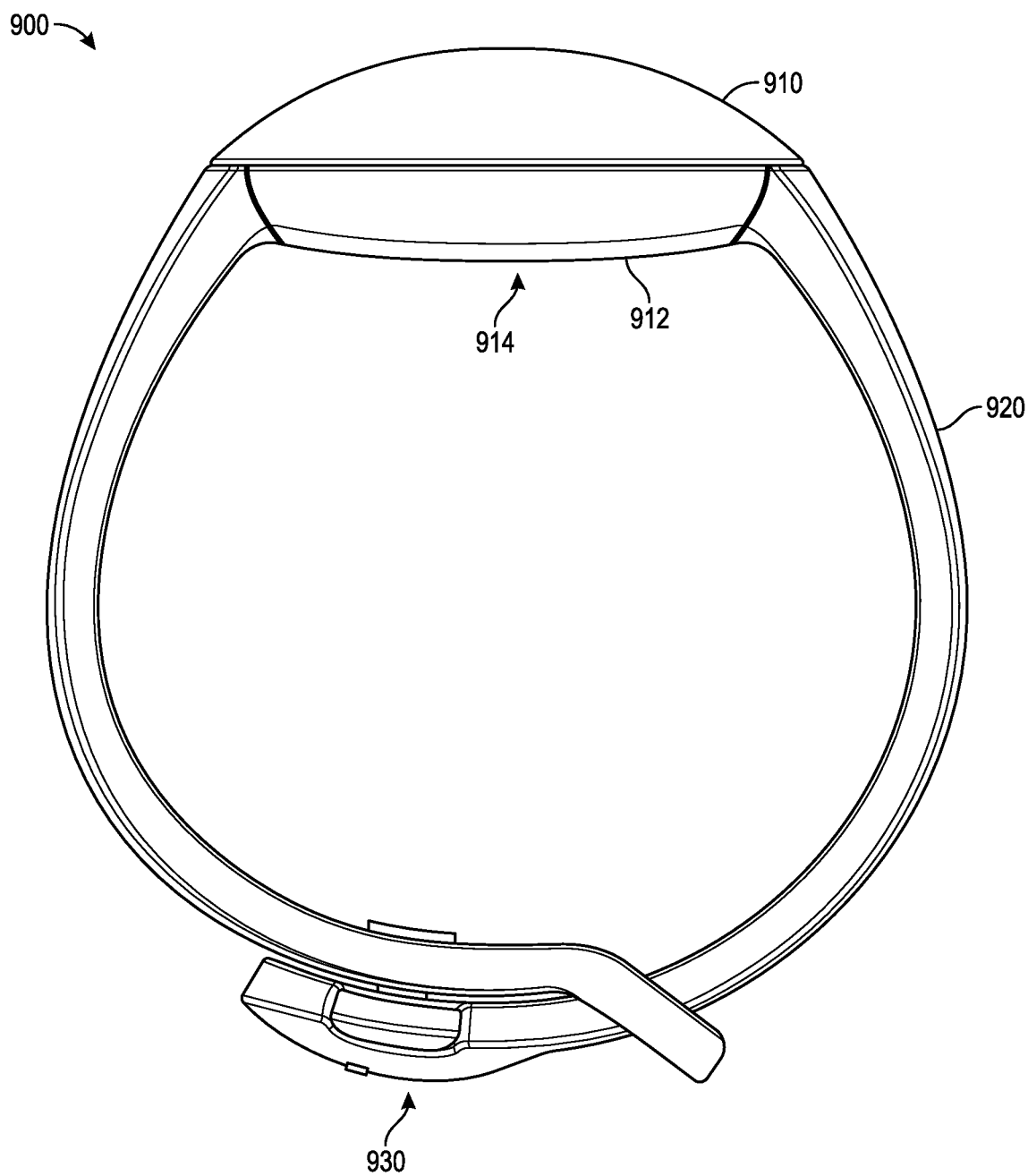

FIGS. 9A-9C are an isometric view, a bottom view, and a side view, respectively of a wearable device 900 for use by a supervised person in accordance with some implementations of the present technology. The wearable device 900 can include the subsystem 800 discussed above with respect to FIG. 8. Further, the wearable device 900 can be deployed as the wearable device 132 discussed above with respect to the system 100 of FIG. 1. As illustrated in FIGS. 9A-9C, the wearable device 900 includes and electronics housing 910 and a flexible strap 920 attached to the electronics housing 910. The electronics housing 910 is designed to sin on top of a wrist and/or on an ankle of the supervised person. Meanwhile, the flexible strap 920 is designed to wrap around the supervised person's wrist and/or ankle to secure the electronics housing on the supervised person. In the illustrated implementation, the wearable device 900 also includes a connecting element 930 on the flexible strap 920 with allows the tightness of the flexible strap 920 around the supervised person's wrist and/or ankle to be adjusted.

In some implementations, the connecting element 930 includes childproof features that prevent the supervised person from removing the wearable device 900. For example, in the illustrated implementation, the connecting element 930 includes a peg and clasp connection that requires force to be applied on two pinchable elements 932 (FIG. 9B) while a peg 934 (FIG. 9A) is pulled outwards. As a result, the connecting element 930 requires two hands to undue, thereby preventing the supervised person from removing the wearable device 900 on their own.

As best illustrated in FIG. 9B, the wearable device 900 includes skin-facing sensors 914 on a lower surface 912 of the electronics housing 910. In various implementations, as discussed above, the skin-facing sensors 914 can include a PPG sensor, a skin temperature sensor, one or more accelerometers, skin conductivity sensors, heart-rate variability sensors, resting heart rate sensors, sweat chemical composition sensors, nervous system electrical sensors, air quality sensors, UV exposure sensors, sensors to detect environmental chemicals, blood oxygen and/or pulse oxygen sensors, voice recognition, electrocardiogram (ECG) sensor, pressure sensors, gyroscopes, magnetometers, and/or any other suitable sensor. In some implementations, as best illustrated in FIG. 9C, the lower surface 912 and the skin-facing sensors 914 can protrude outwardly from the electronics housing 910 with a slightly convex shape. The convex shape of the electronics housing 910 can have at least two functions for the wearable device 900. First, babies, toddlers, and young children can have a slight dip on the top of their wrists that can be at least partially matched by the convex shape of the electronics housing 910. As a result, the skin-facing sensors 914 can maintain better contact with the skin of a supervised person wearing the wearable device 900, thereby allowing the skin-facing sensors 914 to obtain more accurate data. Second, the convex shape of the electronics housing 910 provides more internal space for the electronics of the wearable device 900, thereby allowing the longitudinal footprint of the wearable device 900 to be slightly reduced.

The electronics housing 910 can also include one or more on board power sources (not shown) such as various primary and secondary cell batteries. In some implementations, the electronics housing 910 includes a secondary cell battery that stores enough power to operate the wearable device 900 (and the subsystem thereon), for between about three and about seven days. The long battery life allows the wearable device to be worn to sleep some nights, thereby allowing the skin-facing sensors 914 to continue to collect bioindicator data, for example measuring how well the supervised person is sleeping. In some implementations, the secondary cell battery is fully charged in a period of about an hour, allowing the wearable device to be fully recharged various daily activities that may require removal anyway (e.g., while the supervised person showers). In various implementations, the secondary cell battery can be charged by a wireless charging system (e.g., through inductive chargers) and/or through various cord-based chargers.

Figure 10A:
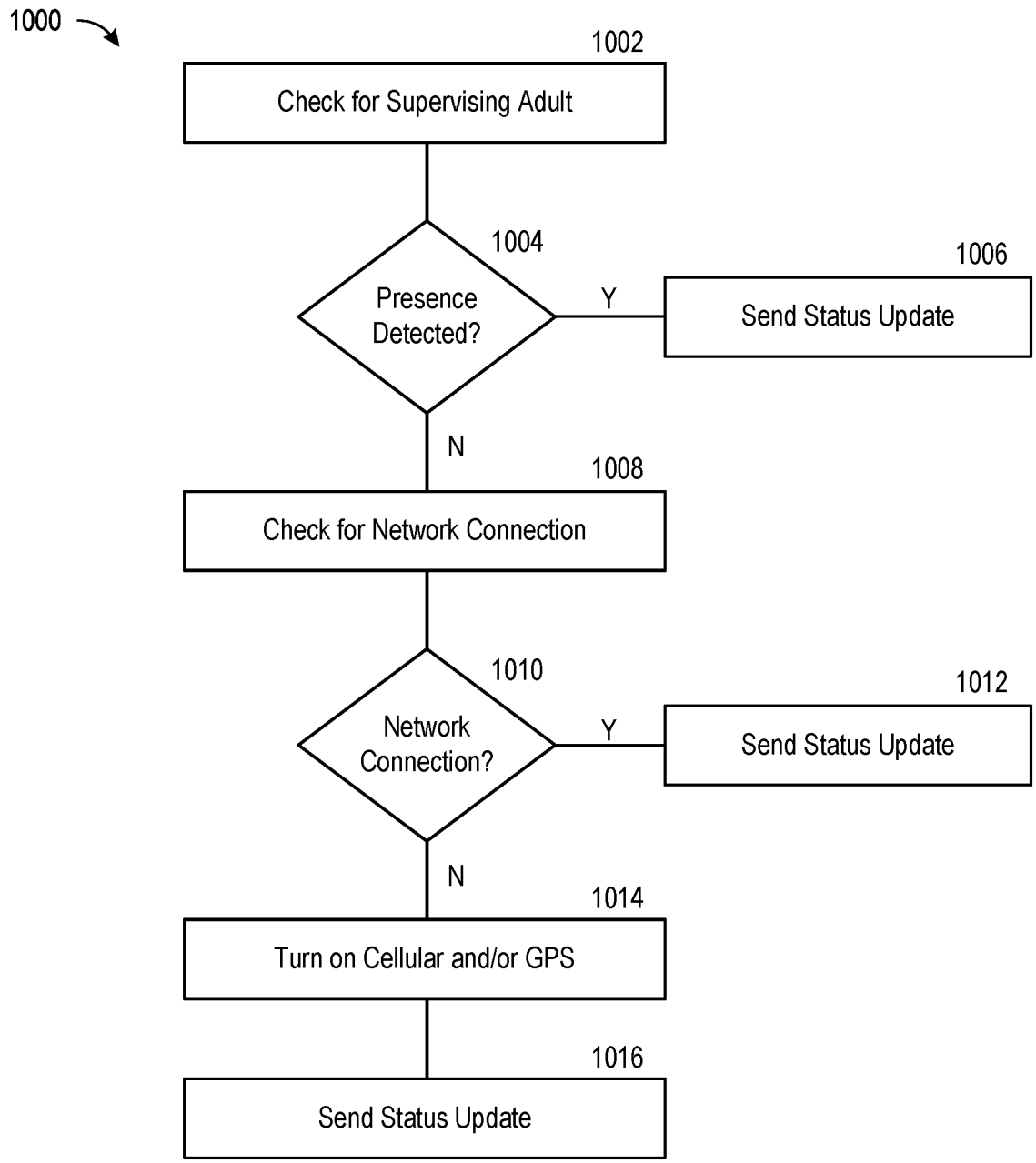
FIG. 10A is a flow diagram of a process for uploading status updates related to a supervised person in accordance with some implementations of the present technology.

FIG. 10A is a flow diagram of a process 1000 for uploading status updates related to a supervised person in accordance with some implementations of the present technology. The process 1000 can be executed by the subsystem 800 discussed above with respect to FIG. 8 (e.g., operating in the wearable device 132 of FIG. 1) to establish communication between the subsystem 800 and another database (e.g., the remote server 140 of FIG. 1) and/or another subsystem (e.g., the subsystems 300, 400 of FIGS. 3 and 4).

The process 1000 begins at block 1002 to check for the presence of a responsible person, such as a controlling person and/or a supervising person, by searching for one of the subsystems 300, 400 of FIGS. 3 and 4. The presence of the responsible person allows the wearable device to communicate the status updates locally using a shortrange communication component (e.g., Bluetooth®) with instructions to forward the status updates to another subsystem (e.g., to the cloud server). In various implementations, checking for the presence of a responsible person can include sending a presence detection signal, checking whether a known device is within a proximity of a shortrange communication component, and/or checking available devices for the device associated with the responsible person.

At decision block 1004, the process 1000 determines whether the presence of the responsible person was detected. If the presence of responsible person was detected, the process 1000 continues to block 1006; else the process continues to block 1008.

At block 1006, the process 1000 includes sending a status update to the responsible person using the shortrange communication component. The status update can include any sensor data that was measured since the last status update, an analysis of the sensor data, an assessment of the condition of the supervised person based on the sensor data, information about the wearable device system (e.g., remaining battery life), and/or any other suitable information. The responsible person can then review the status update and/or forward the status update to a network-connected database (e.g., the remote server 140 of FIG. 1) to be stored. Once stored in the network-connected database, the data from the status update can be reviewed by the controlling persons and/or the supervising persons; analyzed by one or more components of the system (e.g., one or more modules in the cloud sever, accessed by a third party, and the like); and the like.

In some implementations, once the status update has been sent at block 1006, the process 1000 restarts at block 1002. The process 1000 can restart after any suitable time interval (e.g., after one minute, after five minutes, after ten minutes, every half hour, every hour, and/or any other suitable time interval), or can restart instantaneously after sending a status update to continuously send status updates.

As discussed above, the shortrange communication component can use less energy than other components to upload the status updates. Accordingly, as discussed above in reference to FIG. 8, the subsystem 800 can keep other communication components powered off to save battery as long as the presence of the responsible person is detected. Accordingly, using the responsible person to relay the status update to the network-connected database can improve the battery life of the subsystem 800.

At block 1008, the process 1000 includes checking for a network connection, such as a connection to a wireless network. In some implementations, checking for a network connection includes powering an internet communication component (e.g., a WNIC) on then searching for a trusted network connection (e.g., a trusted WiFi connection).

At decision block 1010, the process 1000 the process 1000 determines whether the network connection was detected. If the network connection was detected, the process 1000 continues to block 1012; else the process continues to block 1014.

At block 1012, the process 1000 includes sending the status update using the network connection. The status update can be sent to the responsible person and/or a network-connected database through the network connection. In some implementations, for example, the process 1000 includes sending the status update to the responsible person through the network connection. The responsible person can then review the status update and/or forward the status update to the network-connected database. In some implementations, the process 1000 includes sending the status update directly to the network-connected database. The responsible person can then review the status update through the network-connected database.

As discussed above, once the status update has been sent, the process 1000 can restart at block 1002. In various implementations, the process 1000 can restart after any suitable time interval, or can restart instantaneously after sending a status update to continuously send status updates. In some implementations, the internet communication component remains on until a shortrange wireless connection is detected to efficiently send subsequent status updates.

If no network connection is detected (e.g., because the subsystem 800 is out of range of a wireless connection and/or no wireless connection has been set up), the process 1000 includes turning on a cellular component within at block 1014. As discussed above, powering on the cellular component only after no shortrange connection and no wireless connection is detected can help improve the battery life of a wearable device. Once powered on, the subsystem 800 connects to the network-connected database using the cellular component (e.g., using a 3G connection, 4G connection, LTE connection, 5G connection, 6G connection, and/or any other suitable cellular connection).

At block 1016, the process 1000 includes sending the status update using the cellular component. The status update can be sent to the responsible person to be reviewed and/or forwarded to the network-connected database, and/or can be sent directly to the network-connected database to be reviewed and accessed later.

As discussed above, once the status update has been sent, the process 1000 restarts at block 1002. In various implementations, the process 1000 can restart after any suitable time interval, or can restart instantaneously after sending a status update to continuously send status updates. In some implementations, the cellular component remains on until either a shortrange wireless connection and/or a network connection is detected to efficiently send subsequent status updates.

Figure 10B:
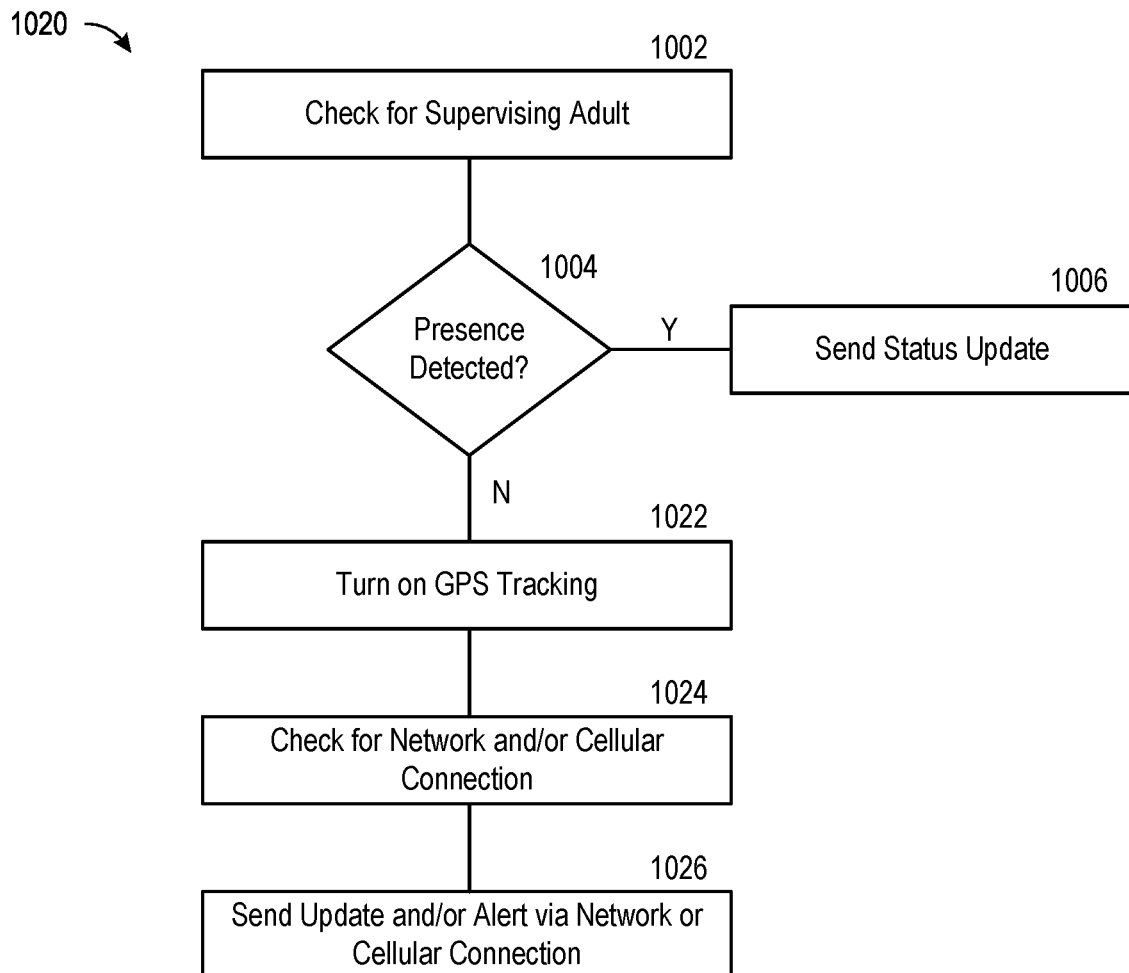
FIG. 10B is a flow diagram of a process for monitoring control a supervised person in accordance with some implementations of the present technology.

FIG. 10B is a flow diagram of a process 1020 for monitoring control over a supervised person in accordance with some implementations of the present technology. The process 1020 can be executed by the subsystem 800 discussed above with respect to FIG. 8 (e.g., operating in the wearable device 132 of FIG. 1) to ensure a supervising person (e.g., associated with the subsystems 300, 400 of FIGS. 3 and 4) is constantly either within a proximity to have control over the supervised or alerted to location of the supervised person.

Similar to the process 1000 of FIG. 10A, the process 1020 begins at block 1002 to check for the presence of a responsible person, such as a controlling person and/or a supervising person, by searching for one of the subsystems 300, 400 of FIGS. 3 and 4. The presence of the responsible person can indicate that the responsible person has control over the supervised person. In various implementations, checking for the presence of a responsible person can include sending a presence detection signal, checking whether a known device is within a proximity of a shortrange communication component, checking available communication devices for the device associated with the responsible person, and/or comparing a shared geographic location of the responsible person to a geographic location of the supervised person to check that the responsible person is within a predetermined proximity (e.g., a distance set by the controlling person) of the supervised person.

At decision block 1004, the process 1000 determines whether the presence of the responsible person was detected. If the presence of responsible person was detected, the process 1000 continues to block 1006; else the process continues to block 1022.

At block 1006, the process 1000 includes sending a status update to the responsible person using the shortrange communication component and/or any other suitable component. As discussed above, the status update can include any sensor data that was measured since the last status update, an analysis of the sensor data, an assessment of the condition of the supervised person based on the sensor data, information about the wearable device system (e.g., remaining battery life), and/or any other suitable information. The responsible person can then review the status update and/or forward the status update to a network-connected database (e.g., the remote server 140 of FIG. 1) to be stored. Additionally, the status update can include instructions to update a record of the control over the responsible person (e.g., held by the cloud server). Once stored in the network-connected database, the data from the status update can be reviewed by the controlling persons and/or the supervising persons; analyzed by one or more components of the system Once stored in the network-connected database, the data from the status update can be reviewed by the controlling persons and/or the supervising persons; analyzed by one or more components of the system (e.g., one or more modules in the cloud sever, accessed by a third party, and the like); and the like. Purely by way of example, the record of control can help track when a supervised person was last under the control of the responsible person whenever they lose control, allowing the responsible person (or any other suitable party) to help locate the supervised person.

At block 1022, the process 1020 includes activating GPS tracking to help track the exact location of the supervised person while they are separated from the responsible person. In some implementations, the GPS component in the wearable device is inactive while the supervised person is under the control of the responsible person. In such implementations, the wearable device can conserve energy consumed by the GPS component until it is needed. Then, at block 1022, activating the GPS tracking can include turning the GPS component on. Additionally, the GPS tracking can include packaging GPS data into each status update sent from the wearable device and/or creating an independent stream of the GPS data to provide real-time (or near real-time) indications of the geographic location of the supervised person.

At block 1024, the process 1020 includes checking for a network and/or cellular connection. As discussed above, the checks can occur sequentially. For example, in some implementations of block 1024, the process 1020 includes checking for a network connection by powering an internet communication component (e.g., a WNIC) on, then searching for a trusted network connection (e.g., a trusted WiFi connection). If no network connection is detected (e.g., because the wearable device is out of range of a wireless connection and/or no wireless connection has been set up), the process 1020 includes turning a cellular component on and connecting to the cloud server using the cellular component (e.g., using a 3G connection, 4G connection, LTE connection, 5G connection, 6G connection, and/or any other suitable cellular connection).

At block 1026, the process 1020 includes sending an update on the geographic location of the wearable device to the cloud server using the network and/or cellular connection. In some implementations, the update also includes data from the sensor(s) on the wearable device, an analysis based on the data from the sensor(s), and the like. The updates can be sent to the cloud server to make the updates viewable by a variety of responsible persons and/or accessible (or shareable) to a third party (e.g., a police or fire department). In some implementations, the process 1020 includes sending continuous updates (e.g., every millisecond, every half second, every second, every five seconds, every thirty seconds, and/or after any other suitable period) to provide real time (or near real time) information on the location of the supervised person.

Additionally, or alternatively, at block 1026, the process 1020 includes sending an alert through the network and/or cellular connection. In some implementations, the alert is sent to the cloud server, which can then take action to alert one or more responsible persons (e.g., the responsible person currently in control over the supervised person, another supervising person, a parent or other legal guardian, an emergency contact, and the like) to the separation between the responsible person and the supervised person and/or to the location of the supervised person. In some implementations, the alert is sent directly to one or more responsible persons (e.g., sending a text message to the currently responsible person and/or a parent or other legal guardian). The alert can then, for example, prompt the one or more responsible persons to track the geographic location of the supervised person.

Figure 10C:
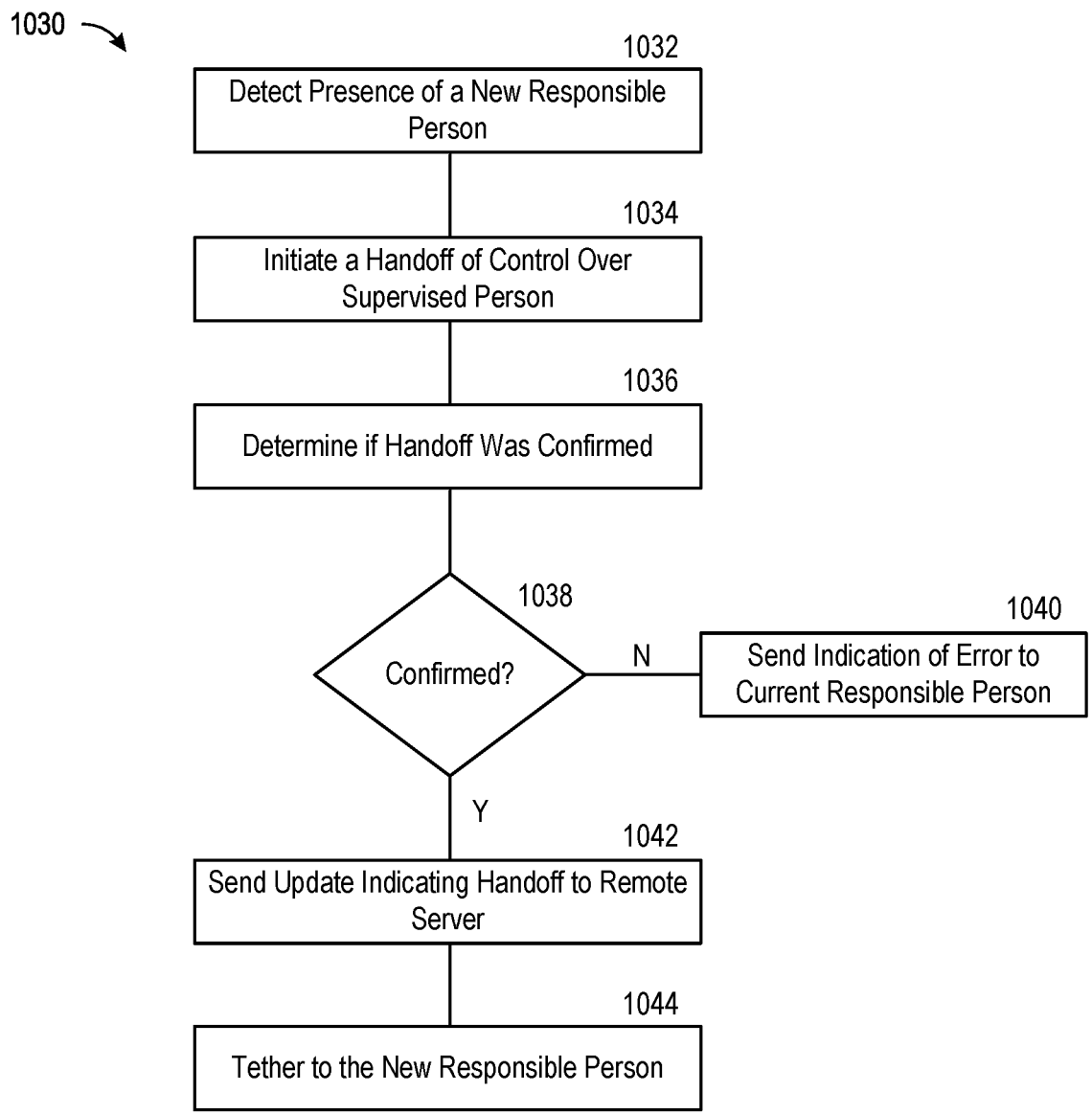
FIG. 10C is a flow diagram of a process for facilitating a handoff of control over a supervised person in accordance with some implementations of the present technology.

FIG. 10C is a flow diagram of a process 1030 for facilitating a handoff of control over a supervised person in accordance with some implementations of the present technology. The process 1030 can be executed by the subsystem 800 discussed above with respect to FIG. 8 (e.g., operating in the wearable device 132 of FIG. 1) to help facilitate a handoff of control over (e.g., responsibility for supervision of) the supervised person. Purely by way of example, the process 1030 can be executed when a parent drops their child off at daycare, when a daycare rotates care providers, and/or when a parent comes to pick their child up from daycare.

The process 1030 begins at block 1032 with detecting a presence of a new responsible person. The presence can be detected through the shortrange communication component in the wearable device and a corresponding shortrange communication component associated with the new responsible person (e.g., via the shortrange communication component in the responsible person's phone and under the control of one of the subsystems 300, 400 of FIGS. 3 and 4). In some implementations, the detection process of block 1032 is generally similar to he checking process described above with reference to block 1002 (e.g., FIG. 10A). Purely by way of example, the wearable device can send periodically out a presence detection signal, then detect the presence of a new responsible person when a response is received from a new subsystem. As a result, the process 1030 can detect when a new responsible person is within a vicinity (e.g., in range of the shortrange communication component) of the supervised person.

At block 1034, the process 1030 includes initiating a handoff of the control over the supervised person from a first responsible person (e.g., a currently responsible person) to a second responsible person (e.g., the new responsible person). In various implementations, initiating the handoff can include sending a prompt to the first responsible person indicating the presence of the second responsible person within a vicinity of the supervised person and/or sending a prompt to the second responsible person indicating the presence of the supervised person and their current assignment to the first responsible person. The prompt can confirm that the first supervising person wants to handoff control over the supervised person to the second responsible person; confirm that the second responsible person wants to accept control over the supervised person; and/or receive an indication from the first and/or second responsible person declining the handoff.

At block 1036, the process 1030 includes determining if the handoff was confirmed. IN some implementations, the wearable device receives a notification from the first and/or second responsible person when the handoff is complete. In such implementations, the notification can help the wearable device keep track of who to send status updates to (e.g., using the process 1000 of FIG. 10A) and/or whose presence to check for (e.g., using the process 1020 of FIG. 10B). In some implementations, the wearable device sends a prompt to one of the first and/or second responsible persons to confirm whether the handoff was complete. In some implementations, if either of the first and/or second responsible persons fail to respond to the prompt (or any ensuing messages) within a predetermined time (e.g., a timeout period), the process 1030 can send a second prompt and/or determine that the handoff was not confirmed. In some implementations, the wearable device checks a record of control at the cloud server to determine whether the handoff was confirmed.

At decision block 1038, the process 1030 checks whether the handoff was confirmed. If the handoff was confirmed, the process 1030 continues to block 1040; else the process continues to block 1042.

At block 1040, responsive to determining that the handoff was not confirmed, the process 1030 includes sending an indication of an error to the first responsible person. The indication of the error alerts the first responsible person that no handoff occurred (e.g., thereby confirming that they still have control over the supervised person). Additionally, the indication of the error can include a cause for the error in the handoff, such as the handoff timing out based on a slow response from the second responsible person, the second responsible person declining the handoff, the supervised person becoming too far away from the second responsible person, and the like. In some implementations, the indication of the error also includes a prompt allowing the first supervising person to send a new request for the handoff.

At block 1042, responsive to determining the handoff was confirmed, the process 1030 includes sending an update indicating the handoff to the cloud server (e.g., via a shortrange message to the second responsible person with instructions to forward the update and/or in a direct message via a network and/or cellular communication component). The update can prompt the cloud server to update a record of control over the supervised person to reflect the handoff. As a result, purely by way of example, a third responsible person (e.g., a parent) can view the handoff (e.g., between two daycare providers) to monitor and/or review who is responsible for a child.

At block 1044, the process 1030 includes tethering the wearable device (and the subsystem thereon) to the second responsible person (e.g., to the subsystem in the second responsible person's smartphone). Tethering to the second responsible person can change which responsible person status updates are sent to, which responsible person is searched for to monitor control over the supervised person, and/or which responsible person is alerted by detected events and/or detected separations. In some implementations, the process 1030 implements block 1044 before implementing block 1042. In some implementations, the process 1030 implements block 1042 and block 1044 generally simultaneously.

Figure 11A:
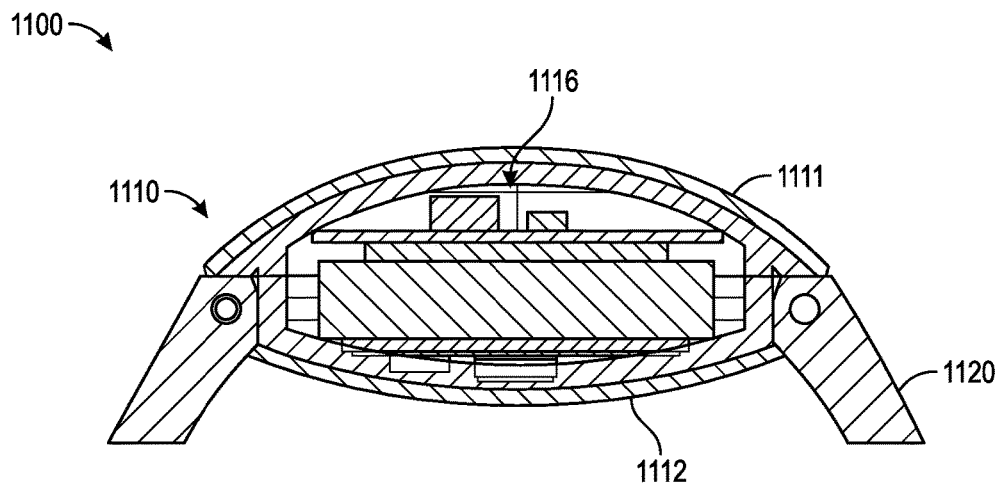
FIGS. 11A and 11B are a cross-sectional and an isometric view, respectively, of a wearable device for use by a supervised person in accordance with some implementations of the present technology.
Figure 11B:
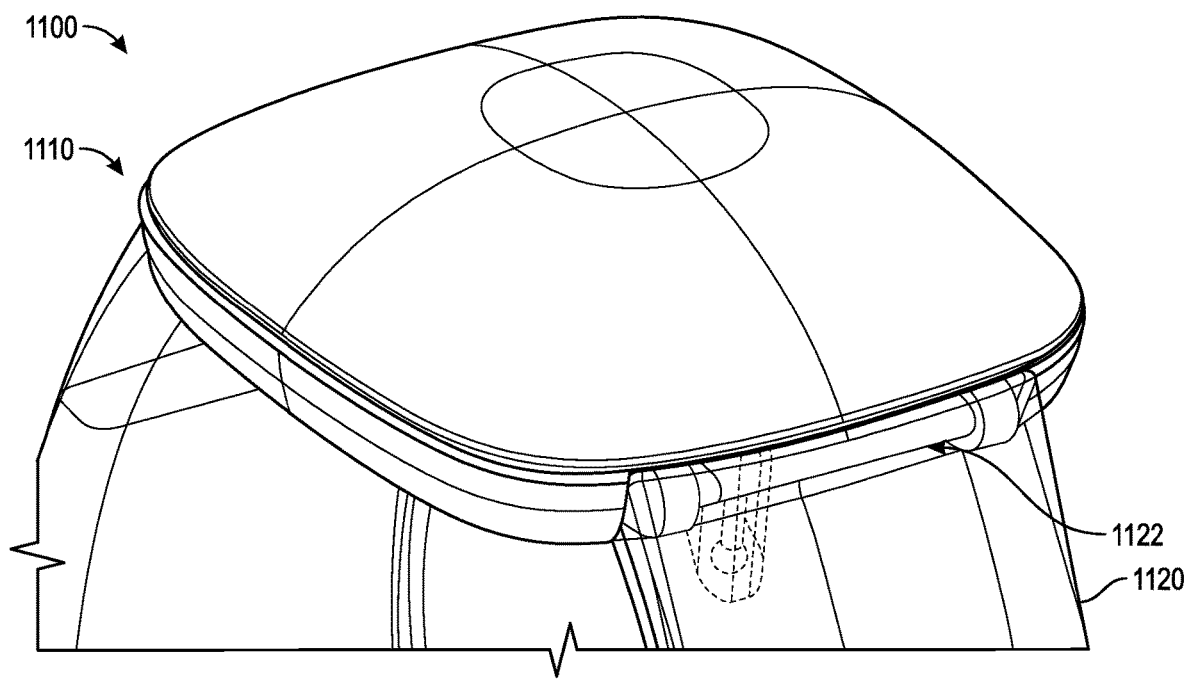

FIGS. 11A and 11B are a cross-sectional and an isometric view, respectively, of a wearable device 1100 for use by a supervised person in accordance with some implementations of the present technology. FIGS. 11A and 11B illustrate additional details on the organization of components within the wearable device 1100. For example, as illustrated, the wearable device 1100 includes an electronics housing 1110 that includes an upper portion 1111 and a lower portion 1112 joined to the upper portion 1111, thereby creating an internal space for electronics 1116 that is protected from physical impacts and/or potential contaminants (e.g., water, dirt, sweat, and the like).

In some implementations, the upper portion 1111 and the lower portion 1112 are joined by ultrasonic welder. The ultrasonic welder can create a strong, complete seal between the upper portion 1111 and the lower portion 1112 without the use of any potentially harmful chemicals at the joint. As a result, the electronics housing 1110 can be sealed from contaminants without introducing a potential source of harm to a supervised person wearing the wearable device 1100. Further, because the ultrasonic welder does not require additional materials to seal the joint between the upper portion 1111 and the lower portion 1112, the ultrasonic welding process can help save space for the electronics 1116. In various implementations, the upper portion 1111 and the lower portion 1112 can be joined by a compression bonding process, an O-ring connection, and/or an adhesive bonding process.

As further illustrated in FIGS. 11A and 11B, the electronics housing 1110 is connected to a flexible strap 1120 by a spring bar component 1122. Spring bars are commonly used to join watch faces to wrist straps because they form a reliable connection and partially bias the straps toward the wearer's wrist. Accordingly, for example, the spring bar component 1122 can help facilitate attaching the flexible strap 1120 around the wrist (or ankle) of the supervised person.

Figure 12A:
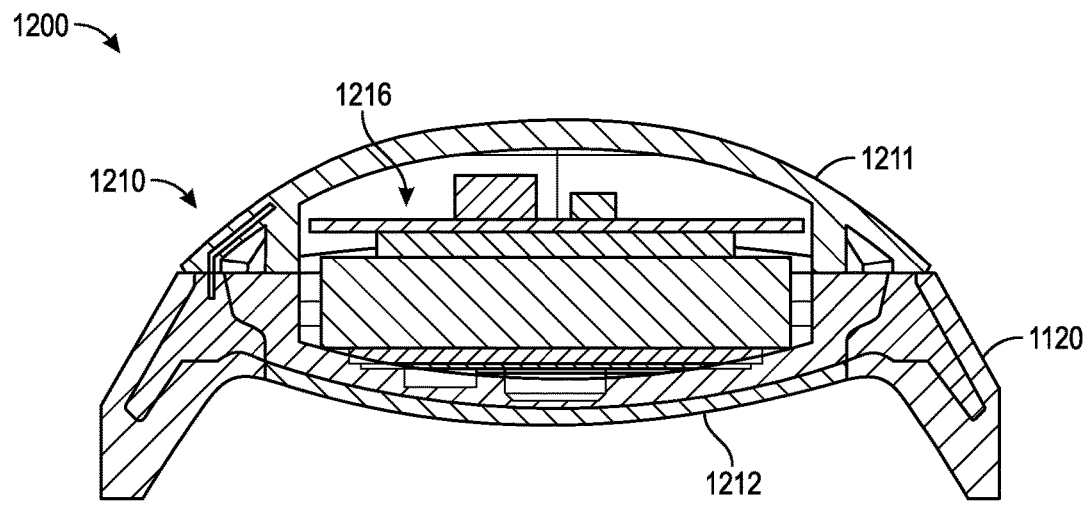
FIGS. 12A and 12B are a cross-sectional and a bottom view, respectively, of a wearable device for use by a supervised person in accordance with some implementations of the present technology.
Figure 12B:
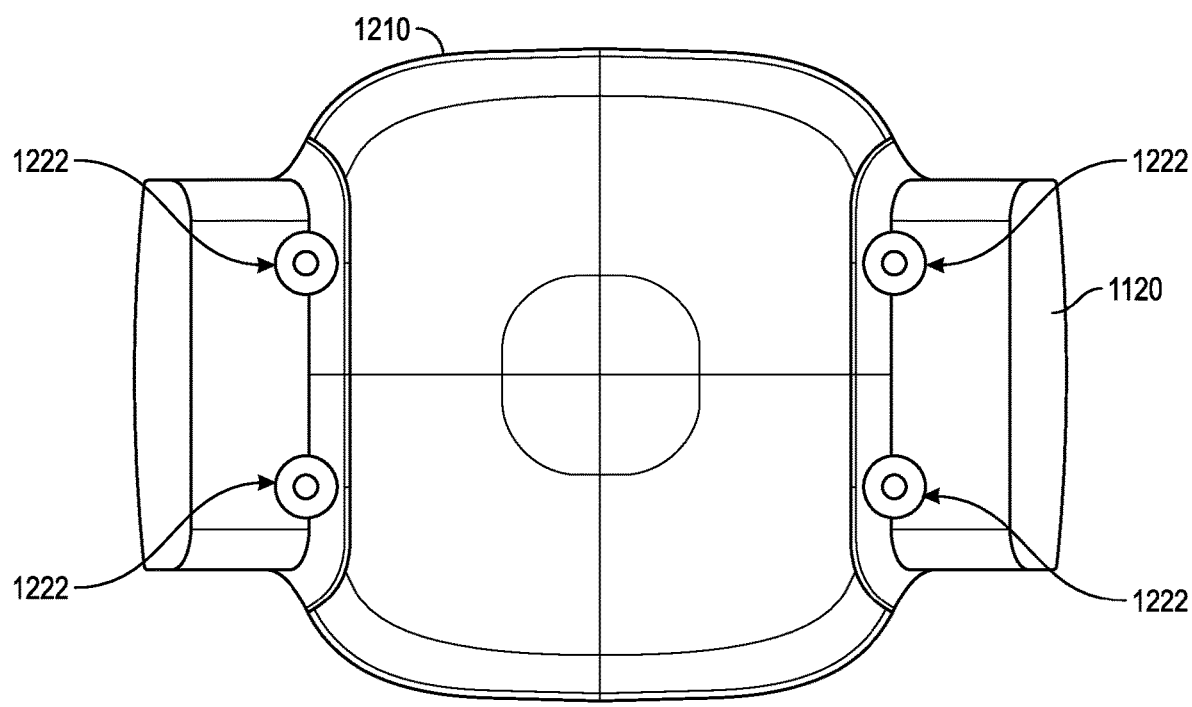

FIGS. 12A and 12B are a cross-sectional and a bottom view, respectively, of a wearable device 1200 for use by a supervised person in accordance with some implementations of the present technology. As illustrated in FIGS. 12A and 12B, the wearable device 1200 is generally similar to the wearable device 1100 discussed above with respect to FIGS. 11A and 11B. For example, the wearable device 1200 includes an electronics housing 1210 with an upper portion 1211 and a lower portion 1212, as well as a flexible strap 1220 connected to the electronics housing 1210. As best illustrated in FIG. 12B, however, the flexible strap 1220 is attached to the electronics housing 1210 with one or more fasteners 1222 (e.g., screws, bolts, pins, and the like). In some implementations, the fasteners 1222 allow the flexible strap 1220 to be quickly and easily swapped, for example to change sizes as the supervised person grows and/or as the flexible strap 1220 wears out. In some implementations, the fasteners 1222 can save space for the electronics 1226 within the electronics housing 1210, thereby helping to reduce the overall footprint of the wearable device 1200.

Suitable Computer Environments

Figure 13:
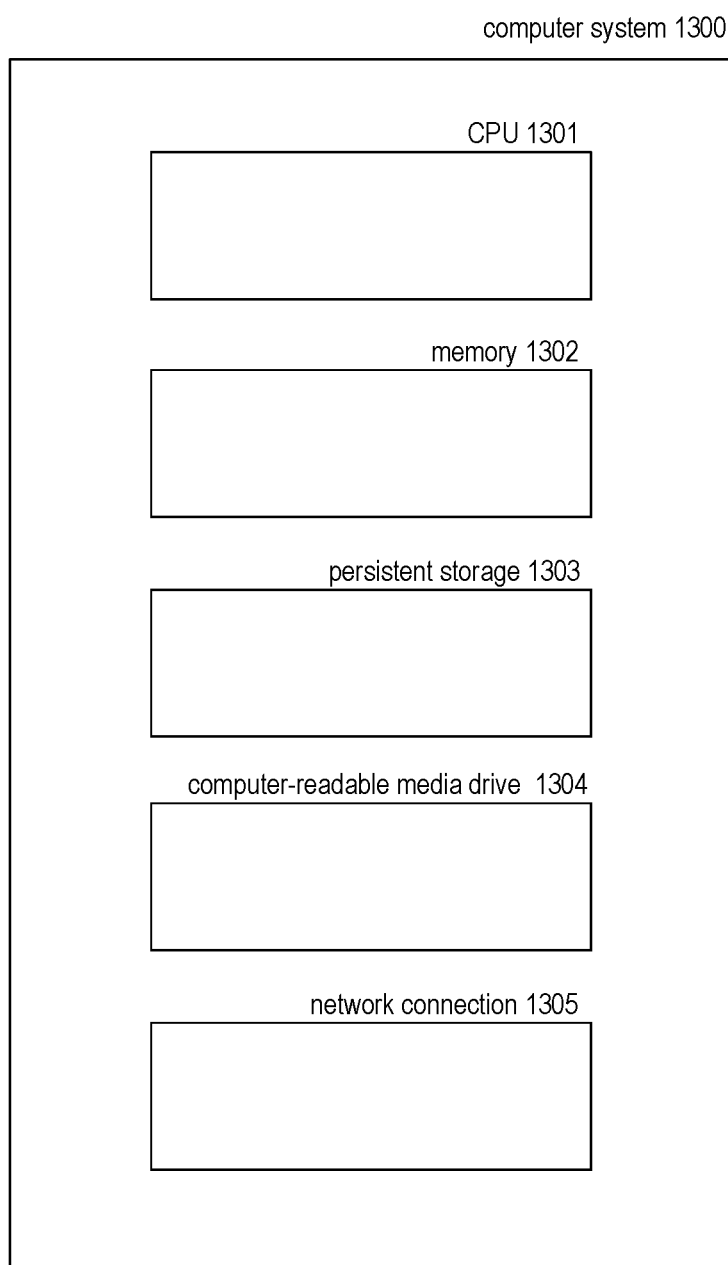
FIG. 13 is a block diagram showing some of the components typically incorporated in at least some of the computer systems and other devices on which the disclosed system operates in accordance with some implementations of the present technology.

FIG. 13 is a block diagram showing some of the components typically incorporated in at least some of the computer systems and other devices on which the disclosed system operates. In various implementations, these computer systems and other devices 1300 can include server computer systems, desktop computer systems, laptop computer systems, netbooks, mobile phones, personal digital assistants, televisions, cameras, unmanned aerial vehicle computers, aerial vehicle computers, satellite computers, electronic media players, etc. In various implementations, the computer systems and devices include zero or more of each of the following: a central processing unit (CPU) 1301 for executing computer programs; a computer memory 1302 for storing programs and data while they are being used, including the facility and associated data, an operating system including a kernel, and device drivers; a persistent storage device 1303, such as a hard drive or flash drive for persistently storing programs and data; computer-readable media drives 1304 that are tangible storage means that do not include a transitory, propagating signal, such as a floppy, CD-ROM, or DVD drive, for reading programs and data stored on a computer-readable medium; and a network connection 1305 for connecting the computer system to other computer systems to send and/or receive data, such as via the Internet or another network and its networking hardware, such as switches, routers, repeaters, electrical cables and optical fibers, light emitters and receivers, radio transmitters and receivers, and the like. While computer systems configured as described above are typically used to support the operation of the facility, those skilled in the art will appreciate that the facility may be implemented using devices of various types and configurations, and having various components.

Figure 14:
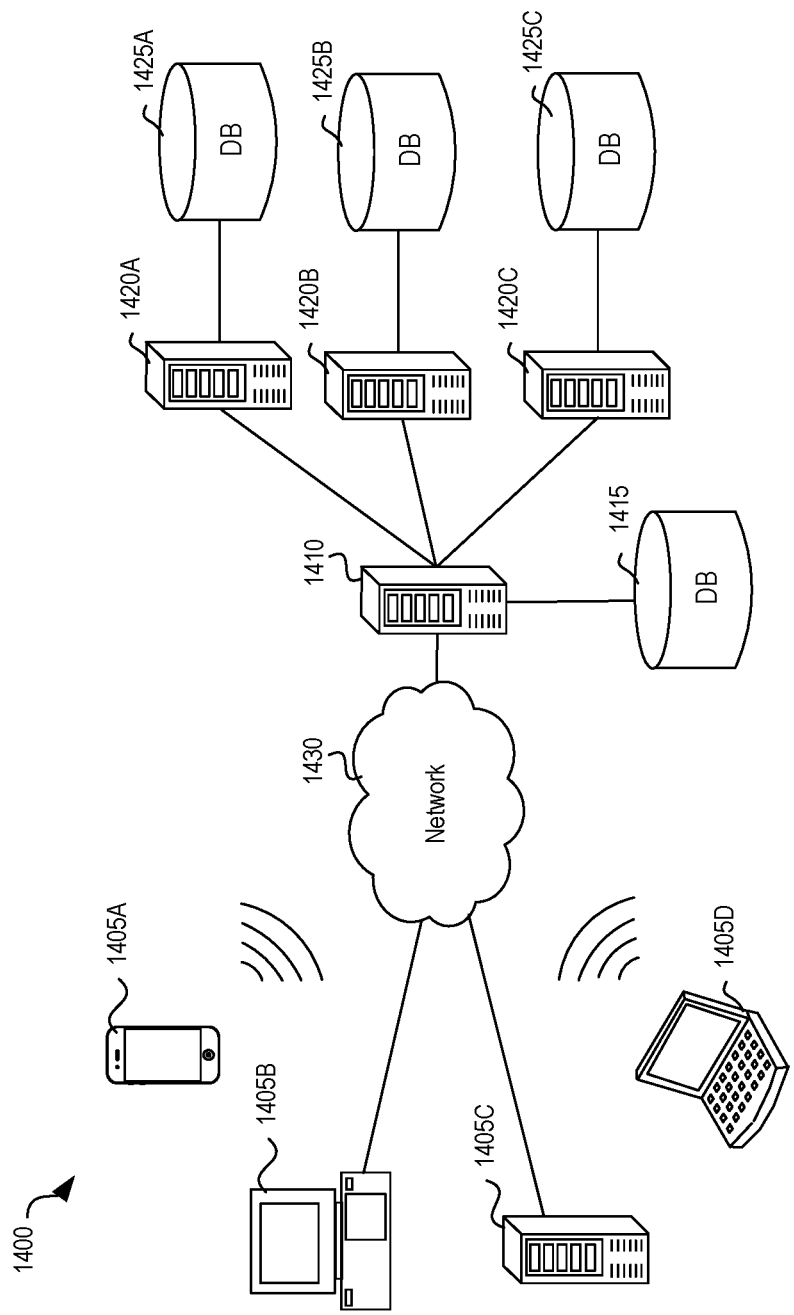
FIG. 14 is a system diagram illustrating an example of a computing environment in which the disclosed system operates in some implementations of the present technology.

FIG. 14 is a system diagram illustrating an example of a computing environment in which the disclosed system operates in some implementations of the present technology. In some implementations, environment 1400 (sometime also referred to as "system 1400") includes one or more client computing devices 1405A-D, examples of which can host the system 1400. Client computing devices 1405 operate in a networked environment using logical connections through network 1430 to one or more remote computers, such as a server computing device.

In some implementations, server 1410 is an edge server which receives client requests and coordinates fulfillment of those requests through other servers, such as servers 1420A-C. In some implementations, server computing devices 1410 and 1420 comprise computing systems, such as the system 1400. Though each server computing device 1410 and 1420 is displayed logically as a single server, server computing devices can each be a distributed computing environment encompassing multiple computing devices located at the same or at geographically disparate physical locations. In some implementations, each server 1420 corresponds to a group of servers.

Client computing devices 1405 and server computing devices 1410 and 1420 can each act as a server or client to other server or client devices. In some implementations, servers (1410, 1420A-C) connect to a corresponding database (1415, 1425A-C). As discussed above, each server 1420 can correspond to a group of servers, and each of these servers can share a database or can have its own database. Databases 1415 and 1425 warehouse (e.g., store) information such as home information, biomass measurements, image measurements, carbon estimates, and so on. Though databases 1415 and 1425 are displayed logically as single units, databases 1415 and 1425 can each be a distributed computing environment encompassing multiple computing devices, can be located within their corresponding server, or can be located at the same or at geographically disparate physical locations.

Network 1430 can be a local area network (LAN) or a wide area network (WAN), or other wired or wireless networks. In some implementations, network 1430 is the Internet or some other public or private network. Client computing devices 1405 are connected to network 1430 through a network interface, such as by wired or wireless communication. While the connections between server 1410 and servers 1420 are shown as separate connections, these connections can be any kind of local, wide area, wired, or wireless network, including network 1430 or a separate public or private network.

EXAMPLES

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A wearable device for improved monitoring of control over a supervised person, the wearable device comprising:
    an electronics housing;

a shortrange wireless component communicably couplable to two or more remote subsystems, the two or more remote subsystems including at least a first remote subsystem and a second remote subsystem;

at least one long range communication component communicably couplable to a remote server; and an operating platform implemented a processor within the electronics housing, wherein the operating platform comprises one or more modules to control the wearable device to:

detect a presence of the second remote subsystem in a vicinity of the wearable device; initiate a handoff of the control over the supervised person from a user of the first remote subsystem to a user of the second remote subsystem; and determine whether a confirmation of the handoff was received from the second remote subsystem, wherein:

responsive to the confirmation of the handoff being received, the operating platform is further configured to send an update indicating the handoff to the remote server to update an indicator of the control over the supervised person, and responsive to the confirmation of the handoff not being received, the operating platform is further configured to send an indication of an error to the user of the first remote subsystem.

2. The wearable device of example 1 wherein initiating the handoff comprises sending a prompt to the user of the first remote subsystem indicating the presence of the second remote subsystem in the vicinity of the wearable device.

3. The wearable device of example 2 wherein the prompt enables the user of the first remote subsystem to send a request for the handoff to the user of the second remote subsystem.

4. The wearable device of any of examples 1-3 wherein initiating the handoff comprises sending a prompt to the user of the second remote subsystem requesting the user of the second remote subsystem to assume control over the supervised person.

5. The wearable device of any of examples 1-4 wherein, when the confirmation of the handoff is received, the operating platform is further configured to tether the wearable device to the second remote subsystem enabling transmission of updates related to the supervised person to the second remote subsystem.

6. The wearable device of example 5 wherein the updates include information related to at least one of: a geographic location of the supervised person, a presence of the supervised person within a preset geofence boundary, a health status of the supervised person, or a developmental status of the supervised person.

7. The wearable device of any of examples 1-6, further comprising one or more sensors carried by the electronics housing and positioned to collect data related to bioindicators, wherein the bioindicators are at least partially indicative of a health and/or developmental status of the supervised person.

8. The wearable device of any of examples 1-7 wherein, when confirmation of the handoff was received, the operating platform is further configured to:

determine a supervision status based on a second detection of the presence of the second remote subsystem within a vicinity of the supervised person;

wherein, when the presence of the second remote subsystem is not identified in the second detection, the operating platform is further configured to send a status update to the remote server via the at least one long range communication component, wherein the status update includes an indication of a lack of control over the supervised person.

9. The wearable device of any of examples 1-8 wherein, when confirmation of the handoff was received, the operating platform is further configured to:

determine a supervision status based on a second detection of the presence of the second remote subsystem within a vicinity of the supervised person;

wherein, when the presence of the second remote subsystem is not identified in the second detection, the operating platform is further configured to send a status update to the first remote subsystem via the at least one long range communication component, wherein the status update includes an indication of a lack of control over the supervised person.

10. The wearable device of any of examples 1-9, further comprising at least one strap coupled to the electronics housing and positioned to secure the wearable device to the supervised person, wherein the at least one strap includes a buckle with a childproof locking mechanism.

11. A non-transitory computer-readable storage medium storing instructions that, when executed by a computing system, cause the computing system to perform operations for monitoring of control over a supervised person, the operations comprising:

detecting a presence of a first user device having a subsystem configured to communicate with a wearable device on the supervised person;

receiving, from a user of a second user device, an indication to generate a handoff request to switch control over the supervised person from the second user device to the first user device;

sending the handoff request to the first user device; and determining whether a confirmation was received from the first user device in response to the handoff request, wherein:

responsive to the confirmation being received, the operations further comprise sending an update indicating an occurrence of the switch of the control over the supervised person to a remote server communicably coupled to the second user device, and responsive to the confirmation not being received, the operations further comprise indicating an error to the user of the second user device.

12. The non-transitory computer-readable storage medium of example 11 wherein the update is configured to alter a chain of custody related to the supervised person stored in the remote server.

13. The non-transitory computer-readable storage medium of any of examples 11 and 12 wherein detecting the presence of the first user device is based on communication between shortrange wireless components in the first user device and the second user device.

14. The non-transitory computer-readable storage medium of any of examples 11-13 wherein the operations further comprise:

receiving, from the user of the second user device, a specification of a geofence boundary and an indication to activate the geofence boundary; and sending, to the remote server, the specification of the geofence boundary and the indication to monitor a geographic location of the wearable device for compliance with the geofence boundary.

15. The non-transitory computer-readable storage medium of example 14 wherein the operations further comprise receiving, from the remote server, a notification indicating a breach of the geofence boundary by the wearable device.

16. The non-transitory computer-readable storage medium of example 15 wherein the operations further comprise receiving, from the first user device, an explanation for the breach.

17. The non-transitory computer-readable storage medium of any of examples 15 and 16 wherein the operations further comprise sending, to the remote server, an indication to deactivate the geofence boundary.

18. A wearable device for monitoring health and development of a supervised person, the wearable device comprising:
   an electronics housing;
   one or more sensors carried by the electronics housing and positioned to collect data related to bioindicators, wherein the bioindicators are at least partially indicative of a health and/or developmental status of the supervised person;
   a shortrange wireless component communicably couplable to at least one remote subsystem;
   at least one long range communication component communicably couplable to a remote server; and
   an operating platform implemented a processor within the electronics housing, wherein the operating platform comprises one or more modules to control the wearable device to:
      receive the data related to the bioindicators from the one or more sensors;
      generate a status update based on the data related to the bioindicators; and check for a presence of the at least one remote subsystem within a communication range of the shortrange wireless component, wherein:
         responsive to the presence of the at least one remote subsystem being detected, the operating platform is further configured to transmit the status update to the detected remote subsystem via the shortrange wireless component; and
         responsive to the presence of the at least one remote subsystem not being detected, the operating platform is further configured to transmit the status update to the remote server via the at least one long range communication component.

19. The wearable device of example 18 wherein the at least one long range communication component has a default mode disconnected from the remote server to conserve energy at the wearable device, and wherein if the presence of the at least one remote subsystem is not detected, the operating platform is further configured to establish a connection between the at least one long range communication component and the remote server before transmitting the status update.

20. The wearable device of any of examples 18 and 19 wherein, if the presence of the at least one remote subsystem is not detected, the operating platform is further configured to transmit an indication of a lack of control over the supervised person to the remote server.

21. The wearable device of any of examples 18-20 wherein, responsive to the presence of the at least one remote subsystem being detected, the status update includes instructions to the at least one remote subsystem for forwarding the status update to the remote server.

22. The wearable device of any of examples 18-21 wherein, responsive to the presence of the at least one remote subsystem being detected, the at least one remote subsystem is configured to:
   receive the status update from the wearable device; and
   transmit the status update to the remote server.

23. The wearable device of any of examples 18-22 wherein the status update includes at least one of (1) the data related to the bioindicators, or (2) an assessment of a current health and/or developmental status of the supervised person based on the bioindicators.

24. The wearable device of any of examples 18-23 wherein generating the status update comprises determining whether any of the bioindicators in the data from the one or more sensors depart from a baseline status for the supervised person.

25. The wearable device of any of examples 18-24 wherein generating the status update comprises determining at least one of: a skin temperature for the supervised person, a skin conductivity for the supervised person, a pulse of the supervised person, and movement of the supervised person.

26. The wearable device of any of examples 18-25 wherein generating the status update comprises determining whether the supervised person experienced a significant physical, emotional, or mental event.

27. The wearable device of any of examples 18-26 wherein the status update includes the data related to the bioindicators from the one or more sensors on the wearable device, and wherein the remote server is configured to:
   process the data from the one or more sensors; and
   update the record of the status of the supervised person based on the processed data.

28. The wearable device of example 27 wherein processing the data from the one or more sensors includes determining whether any of the bioindicators in the data from the one or more sensors depart from a baseline status for the supervised person.

29. The wearable device of any of examples 27 and 28 wherein processing the data from the one or more sensors includes determining at least one of: a skin temperature for the supervised person, a skin conductivity for the supervised person, a pulse of the supervised person, and movement of the supervised person.

30. The wearable device of any of examples 27-29 wherein processing the data from the one or more sensors includes determining whether the supervised person experienced a significant physical, emotional, or mental event.

31. The wearable device of any of examples 18-30 wherein the status update allows the remote server to monitor the health and/or developmental status of the supervised person and recommend one or more supervisory activities to a user of the at least one remote subsystem.

32. The wearable device of any of examples 18-31 wherein the status update allows the remote server to monitor the health and/or developmental status of the supervised person and recommend one or more articles related to child development to a user of the first subsystem and the second subsystem.

33. A system for monitoring control over a supervised person, the system comprising:
   a cloud server having at least one database storing a record of the control over the supervised person;
   a first subsystem communicably coupled to the cloud server through at least one first communication component; and a second subsystem communicably coupled to the cloud server through at least one second communication component, wherein the second subsystem is configured to:
    detect a presence of the first subsystem;
    receive, from a user of the second subsystem, an indication to handoff control over the supervised person from the second subsystem to the first subsystem;
    send a handoff request to the first subsystem; and
    determine whether a confirmation of the handoff request was received from the first subsystem, wherein:
        if the confirmation of the handoff request was received, the second subsystem is further configured to send an update indicating the handoff to the record of the control over the supervised person to the cloud server, and
        if the confirmation of the handoff request was not received, the second subsystem is further configured to indicate an error to the user of the second subsystem.

34. The system of example 33 wherein the cloud server is configured to:
    receive the update indicating the handoff to the record of the control over the supervised person; and
    store an updated record of the control over the supervised person based on the indicated handoff.

35. The system of example 34 wherein the updated record of the control over the supervised person is accessible by the first subsystem and the second subsystem.

36. The system of any of examples 33-35 wherein the first subsystem further includes a first shortrange wireless component, wherein the second subsystem further includes a second shortrange wireless component, and wherein detecting the presence of the first subsystem is based on communication between the first shortrange wireless component and the second shortrange wireless component.

37. The system of any of examples 33-36, further comprising a wearable electronic device configured to be worn by the supervised person, the wearable electronic device comprising:
    an electronics housing;
    a third subsystem carried by electronics carried by the electronics housing, wherein the third subsystem comprises:
        a shortrange wireless component communicably couplable to the first subsystem and the second subsystem to detect a presence at least one of the first subsystem or the second subsystem; and
        at least one third communication component communicably couplable to the cloud server.

38. The system of example 37 wherein the third subsystem is configured to:
    determine a supervision status based on the detection of the presence of at least one of the first subsystem or the second subsystem;
    wherein, when the presence of at least one of the first subsystem or the second subsystem is not detected, the third subsystem is further configured to send a status update to the cloud server via the at least one third communication component, wherein the status update includes an indication of a lack of supervision over the supervised person.

39. The system of any of examples 33-38, further comprising a wearable electronic device configured to be worn by the supervised person, the wearable electronic device including:
    an electronics housing;
    a GPS component carried by the electronics housing; and
    a third subsystem carried by electronics carried by the electronics housing, wherein the third subsystem includes at least one third communication component configured to transmit data from the GPS component to the cloud server.

40. The system of example 39 wherein the cloud server is configured to:
    receive, from one of the first subsystem and the second subsystem, a definition of a geofence boundary and an indication to activate the geofence boundary;
    receive, from the third subsystem, the data from the GPS component; and
    when the data from the GPS component indicates that the electronic device is outside of the geofence boundary, transmit, to at least one of the first subsystem and the second subsystem, a notification of a geofencing breach.

41. The system of any of examples 33-40 wherein the second subsystem is configured to: receive, from the user of the second subsystem, an indication of a geofence boundary; transmit, to the cloud server, an activation signal to enforce the indicated geofence boundary;
    receive, from the cloud server, a notification of a breach of the indicated geofence boundary; and
    receive, from the user of the second subsystem, inputs related to whether the breach of the indicated geofence boundary is explained,
    wherein:
        if the breach of the indicated geofence boundary is explained, the second subsystem is configured to transmit an explanation to the cloud server; and
        if the breach of the indicated geofence boundary is not explained, the second subsystem is configured to transmit an indication of no explanation to the cloud server.

42. The system of example 41 wherein, if the breach of the indicated geofence boundary is explained, the cloud server is configured to deactivate the indicated geofence boundary.

43. The system of any of examples 33-42 wherein the first subsystem is configured to:
    receive, from a user of the first subsystem, an indication of a geofence boundary;
    transmit, to the cloud server, an activation signal to enforce the indicated geofence boundary;
    receive, from the cloud server, a notification of a breach of the indicated geofence boundary; and
    receive, from the user of the first subsystem, inputs related to whether the breach of the indicated geofence boundary is explained,
    wherein:
        if the breach of the indicated geofence boundary is explained, the first subsystem is further configured to transmit an explanation to the cloud server; and
        if the breach of the indicated geofence boundary is not explained, the first subsystem is further configured to transmit a help signal to the second subsystem.

44. The system of any of examples 33-43, further comprising:
    a fourth subsystem communicably coupled to the cloud server through at least one fourth communication component;

wherein the first subsystem is configured to:
  detect a presence of the fourth subsystem;
  receive, from a user of the fourth subsystem, an indication to handoff control over the supervised person from the second subsystem to the fourth subsystem;
  send a second handoff request to the fourth subsystem; and
  determine whether a confirmation of the second handoff request was received from the fourth subsystem, wherein:
    if the confirmation of the second handoff request was received, the first subsystem is further configured to send a second update indicating the record of the control over the supervised person to the cloud server, and
    if the confirmation of the second handoff request was not received, the first subsystem is further configured to indicate an error to the user of the first subsystem.

45. A system for monitoring the health and development of a supervised person, the system comprising:
  a cloud server having at least one database storing a record of a status of the supervised person, wherein the status includes data related to health and development of the supervised person;
  a first subsystem communicably coupled to the cloud server through at least one first communication component;
  a second subsystem communicably coupled to the cloud server through at least one second communication component; and
  a wearable electronic device configured to be worn by the supervised person, the wearable electronic device including:
    an electronics housing;
    one or more sensors carried by the electronics housing and positioned to collect data related to bioindicators, wherein the bioindicators are at least partially indicative of the status of the supervised person; and
    a third subsystem carried by the electronics housing, wherein the third subsystem comprises:
      a shortrange wireless component communicably couplable to the first subsystem and the second subsystem to transmit a status update to at least one of first subsystem or the second subsystem, wherein status update includes the data from the one or more sensors;
      at least one third communication component communicably couplable to transmit the status update to the cloud server.

46. The system of example 45 wherein the third subsystem is further configured to check for a presence of at least one of the first subsystem or the second subsystem within a communication range of the third subsystem using the shortrange wireless component, wherein:
  if the presence of at least one of the first subsystem or the second subsystem is detected within the communication range of the third subsystem, the third subsystem is further configured transmit the status update to the detected subsystem via the shortrange wireless component; and
  if the presence of at least one of the first subsystem or the second subsystem is not detected within the communication range of the third subsystem, the third subsystem is further configured to transmit the status update to the cloud server via the at least one third communication component.

47. The system of example 46 wherein the at least one third communication component has a default mode disconnected from the cloud server to conserve energy at the third subsystem, and wherein if the presence of at least one of the first subsystem or the second subsystem is not detected within the communication range of the third subsystem, the third subsystem is further configured to communicably couple the at least one third communication component to the cloud server before transmitting the status update.

48. The system of any of examples 45-47 wherein the at least one third communication component includes a wireless network communication component and a cellular communication component.

49. The system of any of examples 45-48 wherein, when detected within the communication range of the third subsystem, the first subsystem and the second subsystem are each configured to:
  receive the status update from the wearable device; and
  transmit the status update to the cloud server.

50. The system of any of examples 45-49 wherein the cloud server is configured to:
  receive the status update from the wearable device;
  process the data from the one or more sensors; and
  update the record of the status of the supervised person based on the processed data.

51. The system of example 50 wherein processing the data from the one or more sensors includes determining whether any of the bioindicators in the data from the one or more sensors depart from a baseline status for the supervised person.

52. The system of any of examples 50 and 51 wherein processing the data from the one or more sensors includes determining at least one of: a skin temperature for the supervised person, a skin conductivity for the supervised person, a pulse of the supervised person, and movement of the supervised person.

53. The system of any of examples 50-52 wherein processing the data from the one or more sensors includes determining whether the supervised person experienced a significant physical, emotional, or mental event.

54. The system of any of examples 50-53 wherein the cloud server is further configured to review the record of the status of the supervised person and recommend one or more supervisory activities to a user of the first subsystem and the second subsystem.

55. The system of any of examples 50-54 wherein the cloud server is further configured to review the record of the status of the supervised person and recommend one or more articles related to child development to a user of the first subsystem and the second subsystem.

CONCLUSION

From the foregoing, it will be appreciated that specific implementations of the technology have been described herein for purposes of illustration, but well-known structures and functions have not been shown or described in detail to avoid unnecessarily obscuring the description of the implementations of the technology. To the extent any material incorporated herein by reference conflicts with the present disclosure, the present disclosure controls. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded.

From the foregoing, it will also be appreciated that various modifications may be made without deviating from the disclosure or the technology. For example, one of ordinary skill in the art will understand that various components of the technology can be further divided into subcomponents, or that various components and functions of the technology may be combined and integrated. In addition, certain aspects of the technology described in the context of particular implementations may also be combined or eliminated in other implementations. Furthermore, although advantages associated with certain implementations of the technology have been described in the context of those implementations, other implementations may also exhibit such advantages, and not all implementations need necessarily exhibit such advantages to fall within the scope of the technology. Accordingly, the disclosure and associated technology can encompass other implementations not expressly shown or described herein.

We claim:

1. A wearable device for improved monitoring of control over a supervised person, the wearable device comprising:
    an electronics housing;
    a shortrange wireless component communicably couplable to two or more remote subsystems, the two or more remote subsystems including at least a first remote subsystem and a second remote subsystem;
    at least one long range communication component communicably couplable to a remote server; and
    an operating platform implemented a processor within the electronics housing, wherein the operating platform comprises one or more modules to control the wearable device to:
        detect a presence of the second remote subsystem in a vicinity of the wearable device;
        initiate a handoff of the control over the supervised person from a user of the first remote subsystem to a user of the second remote subsystem; and
        determine whether a confirmation of the handoff was received from the second remote subsystem, wherein:
            responsive to the confirmation of the handoff being received, the operating platform is further configured to send an update indicating the handoff to the remote server to update an indicator of the control over the supervised person, and
            responsive to the confirmation of the handoff not being received, the operating platform is further configured to send an indication of an error to the user of the first remote subsystem.

2. The wearable device of claim 1 wherein initiating the handoff comprises sending a prompt to the user of the first remote subsystem indicating the presence of the second remote subsystem in the vicinity of the wearable device.

3. The wearable device of claim 2 wherein the prompt enables the user of the first remote subsystem to send a request for the handoff to the user of the second remote subsystem.

4. The wearable device of claim 1 wherein initiating the handoff comprises sending a prompt to the user of the second remote subsystem requesting the user of the second remote subsystem to assume control over the supervised person.

5. The wearable device of claim 1 wherein, when the confirmation of the handoff is received, the operating platform is further configured to tether the wearable device to the second remote subsystem enabling transmission of updates related to the supervised person to the second remote subsystem.

6. The wearable device of claim 5 wherein the updates include information related to at least one of: a geographic location of the supervised person, a presence of the supervised person within a preset geofence boundary, a health status of the supervised person, or a developmental status of the supervised person.

7. The wearable device of claim 1, further comprising one or more sensors carried by the electronics housing and positioned to collect data related to bioindicators, wherein the bioindicators are at least partially indicative of a health and/or developmental status of the supervised person.

8. The wearable device of claim 1 wherein, when confirmation of the handoff was received, the operating platform is further configured to:
    determine a supervision status based on a second detection of the presence of the second remote subsystem within a vicinity of the supervised person;
    wherein, when the presence of the second remote subsystem is not identified in the second detection, the operating platform is further configured to send a status update to the remote server via the at least one long range communication component, wherein the status update includes an indication of a lack of control over the supervised person.

9. The wearable device of claim 1 wherein, when confirmation of the handoff was received, the operating platform is further configured to:
    determine a supervision status based on a second detection of the presence of the second remote subsystem within a vicinity of the supervised person;
    wherein, when the presence of the second remote subsystem is not identified in the second detection, the operating platform is further configured to send a status update to the first remote subsystem via the at least one long range communication component, wherein the status update includes an indication of a lack of control over the supervised person.

10. The wearable device of claim 1, further comprising at least one strap coupled to the electronics housing and positioned to secure the wearable device to the supervised person, wherein the at least one strap includes a buckle with a childproof locking mechanism.

11. A non-transitory computer-readable storage medium storing instructions that, when executed by a computing system, cause the computing system to perform operations for monitoring of control over a supervised person, the operations comprising:
    detecting a presence of a first user device having a subsystem configured to communicate with a wearable device on the supervised person;
    receiving, from a user of a second user device, an indication to generate a handoff request to switch control over the supervised person from the second user device to the first user device;
    sending the handoff request to the first user device; and
    determining whether a confirmation was received from the first user device in response to the handoff request, wherein:

responsive to the confirmation being received, the operations further comprise sending an update indicating an occurrence of the switch of the control over the supervised person to a remote server communicably coupled to the second user device, and responsive to the confirmation not being received, the operations further comprise indicating an error to the user of the second user device.

12. The non-transitory computer-readable storage medium of claim 11 wherein the update is configured to alter a chain of custody related to the supervised person stored in the remote server.

13. The non-transitory computer-readable storage medium of claim 11 wherein detecting the presence of the first user device is based on communication between shortrange wireless components in the first user device and the second user device.

14. The non-transitory computer-readable storage medium of claim 11 wherein the operations further comprise:

receiving, from the user of the second user device, a specification of a geofence boundary and an indication to activate the geofence boundary; and sending, to the remote server, the specification of the geofence boundary and the indication to monitor a geographic location of the wearable device for compliance with the geofence boundary.

15. The non-transitory computer-readable storage medium of claim 14 wherein the operations further comprise receiving, from the remote server, a notification indicating a breach of the geofence boundary by the wearable device.

16. The non-transitory computer-readable storage medium of claim 15 wherein the operations further comprise receiving, from the first user device, an explanation for the breach.

17. The non-transitory computer-readable storage medium of claim 15 wherein the operations further comprise sending, to the remote server, an indication to deactivate the geofence boundary.

18. A wearable device for monitoring health and development of a supervised person, the wearable device comprising:

an electronics housing;

one or more sensors carried by the electronics housing and positioned to collect data related to bioindicators, wherein the bioindicators are at least partially indicative of a health and/or developmental status of the supervised person;

a shortrange wireless component communicably couplable to at least one remote subsystem;

at least one long range communication component communicably couplable to a remote server; and an operating platform implemented a processor within the electronics housing, wherein the operating platform comprises one or more modules to control the wearable device to:

receive the data related to the bioindicators from the one or more sensors;

generate a status update based on the data related to the bioindicators; and check for a presence of the at least one remote subsystem within a communication range of the shortrange wireless component, wherein:

responsive to the presence of the at least one remote subsystem being detected, the operating platform is further configured to transmit the status update to the detected remote subsystem via the shortrange wireless component; and responsive to the presence of the at least one remote subsystem not being detected, the operating platform is further configured to transmit the status update to the remote server via the at least one long range communication component.

19. The wearable device of claim 18 wherein the at least one long range communication component has a default mode disconnected from the remote server to conserve energy at the wearable device, and wherein if the presence of the at least one remote subsystem is not detected, the operating platform is further configured to establish a connection between the at least one long range communication component and the remote server before transmitting the status update.

20. The wearable device of claim 18 wherein, if the presence of the at least one remote subsystem is not detected, the operating platform is further configured to transmit an indication of a lack of control over the supervised person to the remote server.

* * * * *